(12) United States Patent
Pei et al.

(10) Patent No.: US 6,887,867 B2
(45) Date of Patent: May 3, 2005

(54) 5H-2,3-BENZODIAZEPINE ANTAGONISTS OF EXCITATORY AMINO ACID RECEPTORS

(75) Inventors: Xue-Feng Pei, Lansdale, PA (US); Baoqing Li, Collegeville, PA (US); Maria-Luisa Maccecchini, West Chester, PA (US)

(73) Assignee: Transgenomic, Inc., Omaha, NE (US)

(*) Notice: Subject to any disclaimer, the term of this patent is extended or adjusted under 35 U.S.C. 154(b) by 143 days.

(21) Appl. No.: 09/882,843

(22) Filed: Jun. 15, 2001

(65) Prior Publication Data

US 2002/0025958 A1 Feb. 28, 2002

Related U.S. Application Data

(60) Provisional application No. 60/212,238, filed on Jun. 16, 2000.

(51) Int. Cl.[7] .............................. A61K 31/55; A61P 9/10; A61P 9/00; C07D 223/14; C07D 243/00
(52) U.S. Cl. ........................ 514/220; 514/221; 540/543; 540/557; 540/567
(58) Field of Search ................................ 514/220, 221; 540/543, 557, 567

(56) References Cited

U.S. PATENT DOCUMENTS

| | | | | |
|---|---|---|---|---|
| 4,614,740 A | * | 9/1986 | Lang et al. | 514/221 |
| 5,716,956 A | | 2/1998 | Pelletier | 514/248 |
| 6,200,970 B1 | * | 3/2001 | Ling et al. | 514/221 |
| 6,323,197 B1 | * | 11/2001 | Csuzdi et al. | 514/219 |

FOREIGN PATENT DOCUMENTS

WO  WO 97/28135  *  8/1997

OTHER PUBLICATIONS

Solyom et al., Non–Competitive AMPA Antagonists of 2,3–Benzodiazepine Type, Current Pharmaceutical Design, vol. 8, No. 10, pp. 913–939, 2002.*

HCAPLUS printout of the species in WO 97/28135.*

Rona et al., Simultaneous Determination of Nerisopam, a Novel Anxiolytic Agent Showing Polymorphic Metabolism, and Its N–Acetyl Metabolite From Human Plasma by a Validated High–Performance Liquid Chromatographic Method, Journal of Chromatography B: Biomedical Applications, vol. 678, No. 1, pp. 63–72, 1996.*

Chen, "Evaluation of five methods for testing anticonvulsant activities," *Proc. Soc. Exp. Biol. Med.* 87:334 (1954).

Donevan & Rogawski, "GYKI 52466, a 2,3–benzodiazephine, is a highly selective, noncompetitive antagonist of AMPA/kainate receptor responses," *Neuron* 10:51–59 (1993).

Hussy, et al., "Functional properties of a cloned 5–hydroxytryptamine Ionotropic receptor subunit: Comparison with native mouse receptors," *J. Physiol.* (London) 481(2):311–323 (1994).

Le Peillet, et al., "The non–NMDA antagonists, NBQX and GYKI 52466, protect against cortical and striatal cell loss following transient global ischaemia in the rat," *Brain Res.* 571:115–120 (1992).

Lipton & Rosenberg, "Excitatory amino acids as a final common pathway for neurologic disorders," *New England Journal of Medicine* 330:613–622 (1994).

McBurney, "Therapeutic potential of NMDA antagoniate in neurodegenerative diseases," *Neurobiology of Aging* 15:271–273 (1994).

Meldrum & Smith, " Cerebroprotective effect of a non–N–methyl–D–aspartate antagonist, GYKI 52466, after focal ischemia in the rat," *Stroke* 23:861 (1992).

Meldrum, "Excitatory amino acids in epilepsy and potential novel therapies," *Epilepsy Research* 12:189–196 (1992).

Remington's Pharmaceutical Sciences 17th Edition, p. 1418 (1985).

Tarnawa, et al., "Electrophysiological studies with a 2,3–benzodiazepine muscle relaxant: GKYI 52466," *Eur. J. Pharmacol* 167:193–199 (1989).

Yamaguchi, et al., "Anticonvulsant activity of AMPA/kainate antagonists: comparison of GYKI 52466 and NBQX in maximal electroshock and chemoconvulsant seizure models," *Epilepsy Research* 15:179–184 (1993).

* cited by examiner

*Primary Examiner*—Brenda Coleman
(74) *Attorney, Agent, or Firm*—Licata & Tyrrell P.C.

(57) ABSTRACT

Substituted benzodiazepine compositions are provided which are active as non-NMDA ionotropic excitatory amino acid (EAA) receptor antagonists. The compounds are generally 7- or 8-mono substituted 5H-2,3-benzodiazepines. The compositions are useful for treating disorders associated with excessive activation of the non-NMDA subtype of the ionotropic EAA receptor. The compounds further are useful as testing agents to identify and characterize other compounds for the treatment of these disorders. The compounds are useful therapeutically as sedatives or for the treatment of neurosychopharmacological disorders such as stroke, ischemia and epilepsy. The compositions may be provided in combination with a suitable carrier for oral or parenteral administration. The compounds may be administered orally or parenterally for the treatment of a variety of disorders associated with non-NMDA EEA receptor function.

12 Claims, 1 Drawing Sheet

5H-2,3-BENZODIAZEPINE ANTAGONISTS OF EXCITATORY AMINO ACID RECEPTORS

CROSS-REFERENCE TO RELATED APPLICATIONS

Priority is claimed to U.S. provisional application Ser. No. 60/212,238, filed Jun. 16, 2000, the teachings f which are incorporated herein

BACKGROUND OF THE INVENTION

This invention relates to mono-substituted 5H-2,3-benzodiazepine compounds useful as antagonists of excitatory amino acid receptors.

During the past twenty-five years a great deal of attention has been directed toward the excitatory amino acids (EAA's), glutamate and aspartate, since they are believed to be the neurotransmitters responsible for the fast excitatory transmission in the mammalian central nervous system. The ionotropic EAA receptors are generally sub-classified into NMDA and non-NMDA receptors. These classifications are defined by those receptors which preferentially bind N-methyl-D-aspartate (NMDA) and those that are not responsive to NMDA but responsive to α-amino-3-hydroxy-5-methyl-4-isoxazoleproprionic acid (AMPA) or kainic acid (KA).

Tarnawa et al, describe 2,3-benzodiazepines (*Eur. J. Pharmacol.*, 167:193–199, 1989) which inhibit AMPA stimulated currents in neuronal cells. The 2,3-benzodiazepines such as GYKI 52466 and 53655 described by Tamawa are non-competitive AMPA antagonists which bind to a novel modulatory site on the AMPA receptor. Meldrum (*Stroke*, 23:861, 1992 & *Brain Res.*, 571:115, 1992) has shown that GYKI 52466 is effective in rat models of both global and focal ischemia. GYKI 52466 was effective in a middle cerebral artery occlusion (MCAO) model of ischemia when given either continuously for 2 hours just after occlusion or delayed for one hour. The compounds reduced cortical infarct volumes by 68% and 48% respectively. In another model of neurodegenerative disease, GYKI 52466 was as effective as the glutamate site competitive antagonist NBQX in rat common carotid arteries model of global ischemia. These two animal models suggest that these compounds may be useful for the treatment of stroke and neurodegenerative ischemic conditions.

Efforts to find NMDA receptor antagonists and blockers which are neuroprotective have been very successful while efforts to find specific non-NMDA receptor antagonists have been much less successful. A number of pharmaceutical companies have pursued development of ion channel blockers or full antagonists of the NMDA receptor to protect against both chronic and acute neurodegenerative processes. Although some compounds have entered clinical trials, there has been only limited progress in developing a clinically useful NMDA receptor antagonist. Some useful compounds, namely substituted dihydrophthalazines, have been described for use as non-NMDA receptor antagonists (U.S. Pat. No. 5,716,956). These compounds are particularly useful because they bind selectively to AMPA receptors. Moreover, 5H-2,3-benzodiazepine AMPA antagonists have been described by Tamawa, et al. (Amino Acids: Chemistry, Biology and Medicine, Lubec, G., Rosenthal, G. A., Eds.; 1990 p. 538).

It is an object of the invention to provide compounds which are useful as non-NMDA glutamate receptor antagonists as well as methods for their synthesis.

It is a further object of the invention to provide non-NMDA receptor antagonists which are useful as sedatives or for the treatment of neuropsychopharmacological disorders such as stroke, ischemia and epilepsy.

It is yet another object of the invention to provide compounds which are useful for the treatment of neurological, neuropsychiatric, neurogenerative and functional disorders associated with excessive activation of the non-NMDA subtypes of the ionotropic EAA receptor.

BRIEF SUMMARY OF THE INVENTION

Compositions are provided which are active as non-NMDA ionotropic excitatory amino acid (EAA) receptor antagonists, in particular, which bind to the AMPA receptors, and which therefore are useful for treating disorders associated with excessive activation of the non-NMDA subtypes of the ionotropic EAA receptors. The compounds further are useful as testing agents to identify and characterize other compounds for the treatment of these disorders. The disclosed compounds are 7- or 8-mono substituted 5H-2,3-benzodiazepines.

Illustrative compounds include:

1-(4-Aminophenyl)-3,5-dihydro-4-methyl-3-acetyl-7-methoxy-5H-2,3-benzodiazepine, 1-(4-Aminophenyl)-3,5-dihydro-4-methyl-3-acetyl-8-methoxy-5H-2,3-benzodiazepine, 1-(4-Aminophenyl)-3,5-dihydro-4-methyl-3-methylcarbamoyl-7-methoxy-5H-2,3-benzodiazepine, 1-(4-Aminophenyl)-3,5-dihydro-4-methyl-3-ethylcarbamoyl-7-methoxy-5H-2,3-benzodiazepine, 1-(4-Aminophenyl)-3,5-dihydro-4-methyl-3-propylcarbamoyl-7-methoxy-5H-2,3-benzodiazepine, 1-(4-Aminophenyl)-3,5-dihydro-4-methyl-3-butylcarbamoyl-7-methoxy-5H-2,3-benzodiazepine, 1-(4-Aminophenyl)-8-amino-3,5-dihydro-4-methyl-3-acetyl-7-methoxy-5H-2,3-benzodiazepine, 1-(4-Aminophenyl)-8-amino-3,5-dihydro-4-methyl-3-methylcarbamoyl-7-methoxy-5H-2,3-benzodiazepine, 1-(4-Aminophenyl)-8-amino-3,5-dihydro-4-methyl-3-ethylcarbamoyl-7-methoxy-5H-2,3-benzodiazepine, 1-(4-Aminophenyl)-8-amino-3,5-dihydro-4-methyl-3-propylcarbamoyl-7-methoxy-5H-2,3-benzodiazepine, 1-(4-Aminophenyl)-8-amino-3,5-dihydro-4-methyl-3-butylcarbamoyl-7-methoxy-5H-2,3-benzodiazepine, 1-(4-Aminophenyl)-3,5-dihydro-4-methyl-3-acetyl-8-methoxy-5H-2,3-benzodiazepine, 1-(4-Aminophenyl)-3,5-dihydro-4-methyl-3-methylcarbamoyl-8-methoxy-5H-2,3-benzodiazepine, 1-(4-Aminophenyl)-3,5-dihydro-4-methyl-3-ethylcarbamoyl-8-methoxy-5H-2,3-benzodiazepine, 1-(4-Aminophenyl)-3,5-dihydro-4-methyl-3-propylcarbamoyl-8-methoxy-5H-2,3-benzodiazepine, 1-(4-Aminophenyl)-3,5-dihydro-4-methyl-3-butylcarbamoyl-8-methoxy-5H-2,3-benzodiazepine, 1-(4-Aminophenyl)-7-amino-3,5-dihydro-4-methyl-3-acetyl-8-methoxy-5H-2,3-benzodiazepine, 1-(4-Aminophenyl)-7-amino-3,5-dihydro-4-methyl-3-methylcarbamoyl-8-methoxy-5H-2,3-benzodiazepine, 1-(4-Aminophenyl)-7-amino-3,5-dihydro-4-methyl-3-ethylcarbamoyl-8-methoxy-5H-2,3-benzodiazepine, 1-(4-Aminophenyl)-7-amino-3,5-dihydro-4-methyl-3-propylcarbamoyl-8-methoxy-5H-2,3-benzodiazepine, 1-(4-Aminophenyl)-7-amino-3,5-dihydro-4-methyl-3-butylcarbamoyl-8-methoxy-5H-2,3-benzodiazepine, 1-(4-Aminophenyl)-3,5-dihydro-4-methyl-3-acetyl-7-methylthio-5H-2,3-benzodiazepine, 1-(4-Aminophenyl)-3,5-dihydro-4-methyl-3-methylcarbamoyl-7-methylthio-5H-2,3-benzodiazepine, 1-(4-Aminophenyl)-3,5-dihydro-4-methyl-3-ethylcarbamoyl-7-methylthio-5H-2,3-benzodiazepine, 1-(4-Aminophenyl)-3,5-dihydro-4-methyl-3-propylcarbamoyl-7-methylthio-5H-2,3-benzodiazepine, 1-(4-Aminophenyl)-3,5-dihydro-4-methyl-3-butylcarbamoyl-7-methylthio-5H-2,3-benzodiazepine, 1-(4-Aminophenyl)-8-amino-3,5-dihydro-4-methyl-3-acetyl-7-methylthio-5H-2,3-benzodiazepine, 1-(4-Aminophenyl)-8-amino-3,5-dihydro-4-methyl-3-methylcarbamoyl-7-methylthio-5H-2,3-benzodiazepine, 1-(4-Aminophenyl)-8-amino-3,5-dihydro-4-methyl-3-ethylcarbamoyl-7-methylthio-5H-2,3-benzodiazepine, 1-(4-Aminophenyl)-8-amino-3,5-dihydro-4-methyl-3-propylcarbamoyl-7-methylthio-5H-2,3-benzodiazepine, 1-(4-Aminophenyl)-8-amino-3,5-dihydro-4-methyl-3-butylcarbamoyl-7-methylthio-5H-2,3-benzodiazepine, 1-(4-Aminophenyl)-3,5-dihydro-4-methyl-3-acetyl-8-methylthio-5H-2,3-benzodiazepine, 1-(4-Aminophenyl)-3,5-dihydro-4-methyl-3-methylcarbamoyl-8-methylthio-5H-2,3-benzodiazepine, 1-(4-Aminophenyl)-3,5-dihydro-4-methyl-3-ethylcarbamoyl-8-methylthio-5H-2,3-benzodiazepine, 1-(4-Aminophenyl)-3,5-dihydro-4-methyl-3-propylcarbamoyl-8-methylthio-5H-2,3-benzodiazepine, 1-(4-Aminophenyl)-3,5-dihydro-4-methyl-3-butylcarbamoyl-8-methylthio-5H-2,3-benzodiazepine, 1-(4-Aminophenyl)-7-amino-3,5-dihydro-4-methyl-3-acetyl-8-methylthio-5H-2,3-benzodiazepine, 1-(4-Aminophenyl)-7-amino-3,5-dihydro-4-methyl-3-methylcarbamoyl-8-methylthio-5H-2,3-benzodiazepine, 1-(4-Aminophenyl)-7-amino-3,5-dihydro-4-methyl-3-ethylcarbamoyl-8-methylthio-5H-2,3-benzodiazepine, 1-(4-Aminophenyl)-7-amino-3,5-dihydro-4-methyl-3-propylcarbamoyl-8-methylthio-5H-2,3-benzodiazepine, 1-(4-Aminophenyl)-7-amino-3,5-dihydro-4-methyl-3-butylcarbamoyl-8-methylthio-5H-2,3-benzodiazepine, 1-(4-Aminophenyl)-4-methyl-7-methoxy-5H-2,3-benzodiazepine, 1-(4-Aminophenyl)-8-amino-4-methyl-7-methoxy-5H-2,3-benzodiazepine, 1-(4-Aminophenyl)-4-methyl-8-methoxy-5H-2,3-benzodiazepine, 1-(4-Aminophenyl)-7-amino-4-methyl-8-methoxy-5H-2,3-benzodiazepine, 1-(4-Aminophenyl)-4-methyl-7-methylthio-5H-2,3-benzodiazepine, 1-(4-Aminophenyl)-8-amino-4-methyl-7-methylthio-5H-2,3-benzodiazepine, 1-(4-Aminophenyl)-4-methyl-8-methylthio-5H-2,3-benzodiazepine, and 1-(4-Aminophenyl)-7-amino-4-methyl-8-methylthio-5H-2,3-benzodiazepine.

The compositions may be provided in combination with a suitable carrier for oral or parenteral administration. The compounds may be administered orally or parenterally for the treatment of a variety of disorders associated with non-NMDA glutamate receptor function. The compositions may be used, for example, as sedatives or for the treatment of neuropsychopharmacological disorders such as stroke, ischemia and epilesy.

DETAILED DESCRIPTION OF THE INVENTION

Figure 1:
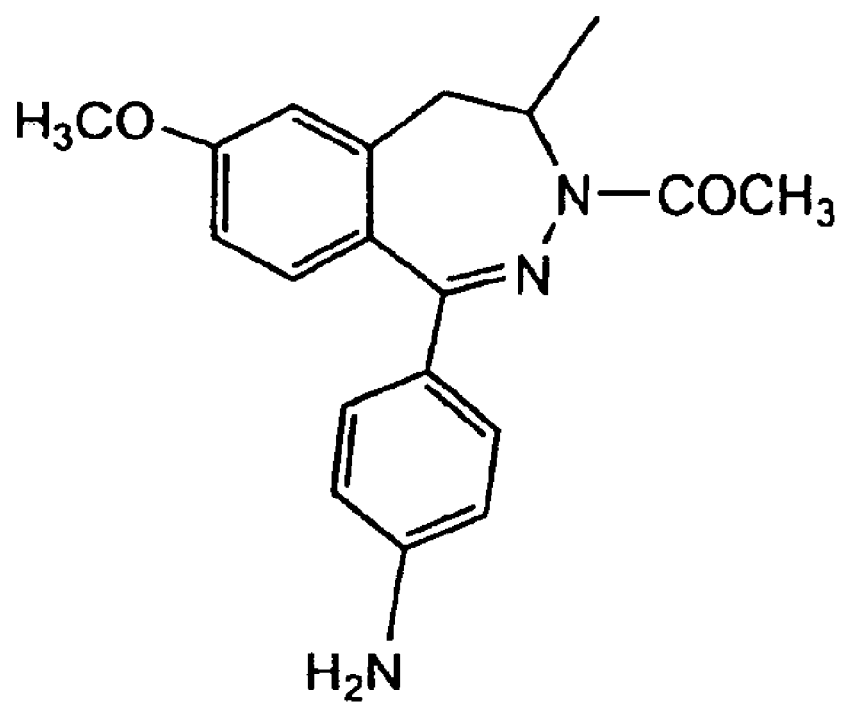
FIG. 1 is a diagram of the structure of SYM 2267, 1-(4-Aminophenyl)-3-acetyl-3,5-dihydro-4-methyl-7-methoxy-5H-2,3-benzodiazepine.

I. Glossary of Terms.

The term "antagonist" as used herein means any compound which reduces the flow of ions through the non-NMDA receptor.

The term "neuropsychopharmacological disorder" as used herein means a disorder resulting from or associated with an excessive flux of ions through the AMPA receptor ligand-gated cation channels, and includes chemical toxicity (including substance tolerance and addiction), excitotoxicity, neurodegenerative disorders (such as Huntington's disease, Parkinson's disease, and Alzheimer's disease), post-stroke sequelae, epilepsy, seizures, mood disorders (such as bipolar disorder, dysthymia, and seasonal affective disorder), and depression. Neurodegenerative disorders can result from dysfunction or malfunction of the AMPA receptor.

The term "NMDA receptor" as used herein means a receptor which is stimulated, at a minimum, by the excitatory amino acids glutamic acid as well as by NMDA, but is not stimulated by AMPA or KA. It is a ligand-gated receptor.

The term "AMPA receptor" as used herein means a receptor which is stimulated, at a minimum, by the excitatory amino acids glutamic acid as well as by AMPA, but is not stimulated by NMDA. It is a ligand-gated receptor.

The term "Kainate receptor" as used herein means a receptor which is stimulated, at a minimum, by the excitatory amino acids glutamic acid as well as by KA, but is not stimulated by NMDA or AMPA. It is a ligand-gated receptor.

The term "activation" as used herein in reference to neurotransmitter receptors means the opening of an ion channel to transfer an electric signal generated by an ion flux through the channel. The activation level of receptors can be altered by the disclosed compounds. The term "excessive activation" refers to an activation that the opening of an ion channel for a prolonged period of time so that there is an excessive ion flux through the channel, which results in substantial damages to the cell including cell death.

Throughout this application when an alkyl substituent is identified, the normal alkyl structure is intended (i.e. butyl is n-butyl) unless otherwise specified. However, when radicals are identified (e.g. $R^5$), both branched and straight chains are included in the definition of alkyl, alkenyl, and alkynyl.

II. Compositions with Non-NMDA Receptor Antagonist Properties.

A. Compounds of Formula I

Compounds of Formula I are provided which are active as non-NMDA ionotropic EAA receptor antagonists.

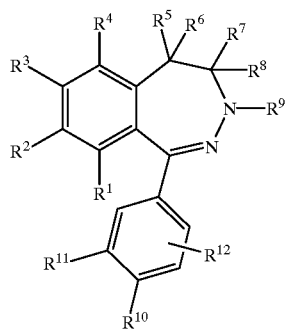

where
- $R^1$, $R^2$, $R^3$ and $R^4$ are independently
  - H,
  - HO,
  - $R^{13}$O—,
  - halogen (F, Cl, Br),
  - C1–C3-alkyl,
  - CF$_3$,
  - $R^{14}$CO$_2$—,
  - $R^{14}$O$_2$C—,
  - $R^{14}$CO—,
  - $R^{14}$CONH—,
  - $R^{14}$NHCO—,
  - $R^{14}$NHCO$_2$—,
  - $R^{14}$OCONH—,
  - $R^{14}$O$_2$S—,
  - $R^{14}$OS—, or
  - $R^{15}R^{16}$N—; or
- $R^1$ and $R^2$, or $R^2$ and $R^3$, or $R^3$ and $R^4$ taken together can be
  - —SCH$_2$S—,
  - —SCH$_2$O—,
  - —OCH$_2$S—,
  - —SCH$_2$CH$_2$S—,
  - —SCH$_2$CH$_2$O—, or
  - —OCH$_2$CH$_2$S—;
- where one of $R^1$, $R^2$, $R^3$ and $R^4$ must be C1–C3-alkoxy or C1–C3-alkylthio group;
- $R^5$, $R^6$, $R^7$, and $R^8$ are independently
  - H,
  - C1–C6-alkyl,
  - C3–C6-alkenyl,
  - C3–C6-cycloalkyl,
  - phenyl or substituted phenyl, where the phenyl is substituted with one or two substituents, C1–C3-alkyl, halogen (F, Cl, Br), $R^{13}$O—, CF$_3$—, $R^{14}$O$_2$S—, $R^{14}$OS—, $R^{14}$CO, $R^{14}$CO$_2$—, $R^{14}$O$_2$C—, $R^{14}$CONH—, $R^{14}$NHCO; or
- $R^5$ and $R^6$ taken together can be C3–C6-cycloalkyl;
- $R^7$ and $R^8$ taken together can be C3–C6-cycloalkyl;
- $R^9$ is
  - $R^{15}R^{16}$NCO—,
  - $R^{15}R^{16}$NCS—,
  - $R^{15}R^{16}$N(CR$^{17}$)—,
  - $R^{17}$OCO—,
  - $R^{15}R^{16}$NCH$_2$CO—,
  - $R^{14}$O$_2$C—(CH$_2$)$_n$—,
  - $R^{15}R^{16}$NCO—(CH$_2$)$_n$—,
  - NC—(CH$_2$)$_n$—,
  - H,
  - C1–C6-alkyl,
  - C3–C6-alkenyl, or
  - C3–C6-cycloalkyl; or
- $R^8$ and $R^9$ taken together can be
  - —(CH$_2$)$_m$CH$_2$(R$^{15}$)NCO—,
  - —(CH$_2$)$_m$CH$_2$OCO—, or
  - —(CH$_2$)$_m$CH$_2$CH$_2$CO—;
- $R^{10}$ and $R^{11}$ are independently
  - H,
  - $R^{15}R^{16}$N—,
  - $R^{15}R^{16}$N(CR$^{17}$)—,
  - $R^{14}$HNCO—, or
  - $R^{14}$CONH—;
- $R^{12}$ is
  - H,
  - halogen (F, Cl, Br),
  - HO,
  - $R^{13}$O—,
  - $R^{15}R^{16}$N—,
  - C1–C3-alkyl,
  - CF$_3$,
  - $R^{14}$CO$_2$—,
  - $R^{14}$CO—, or
  - $R^{14}$CONH—;
- $R^{13}$ is C1–C3-alkyl;
- $R^{14}$ is H or C1–C3-alkyl;
- $R^{15}$ and $R^{16}$ are independently
  - H,
  - C1–C10-alkyl,
  - C1–C6-perfluoroalkyl,
  - C3–C10-alkenyl, or
  - C3–C6-cycloalkyl; or
- $R^{15}$ and $R^{16}$ taken together can be C3–C6-cycloalkyl;
- $R^{17}$ is C1–C6-alkyl, C3–C6-alkenyl, or C3–C6-cycloalkyl;
- n is 1 to 6;
- m is 0 to 2;
- and pharmaceutically acceptable salts thereof;
- where $R^{10}$ and $R^{11}$ cannot be both H.

Preferred compounds are compounds of Formula I where: one of four substituents of $R^1$, $R^2$, $R^3$ and $R^4$ must be C1–C3-alkylthio group or C1–C3-alkoxy group, the other substituents are independently H, $R^{13}$O—, $R^{13}$S—, halogen (F, Cl, Br), or C1–C3-alkyl;

$R^2$ and $R^3$ taken together can be —SCH$_2$S—, —SCH$_2$O—, or —OCH$_2$S—;

$R^9$ is
- $R^{15}R^{16}$NCO—,
- $R^{15}R^{16}$NCS—,
- $R^{15}R^{16}$N(CR$^{17}$)—,
- $R^{17}$OCO—,
- $R^{15}$CO—, or
- H;

$R^{10}$ and $R^{11}$ are independently H, H$_2$N—, or CH$_3$CONH—; and pharmaceutically acceptable salts thereof.

Specifically preferred are:
- 1-(4-Aminophenyl)-3,5-dihydro-4-methyl-3-acetyl-7-methoxy-5H-2,3-benzodiazepine,
- 1-(4-Aminophenyl)-3,5-dihydro-4-methyl-3-acetyl-8-methoxy-5H-2,3-benzodiazepine,
- 1-(4-Aminophenyl)-3,5-dihydro-4-methyl-3-acetyl-7-amino-8-methoxy-5H-2,3-benzodiazepine,
- 1-(4-Aminophenyl)-3,5-dihydro-4-methyl-3-methylcarbamoyl-7-methoxy-5H-2,3-benzodiazepine,
- 1-(4-Aminophenyl)-3,5-dihydro-4-methyl-3-ethylcarbamoyl-7-methoxy-5H-2,3-benzodiazepine,
- 1-(4-Aminophenyl)-3,5-dihydro-4-methyl-3-propylcarbamoyl-7-methoxy-5H-2,3-benzodiazepine,
- 1-(4-Aminophenyl)-3,5-dihydro-4-methyl-3-butylcarbamoyl-7-methoxy-5H-2,3-benzodiazepine,
- 1-(4-Aminophenyl)-8-amino-3,5-dihydro-4-methyl-3-acetyl-7-methoxy-5H-2,3-benzodiazepine,
- 1-(4-Aminophenyl)-8-amino-3,5-dihydro-4-methyl-3-methylcarbamoyl-7-methoxy-5H-2,3-benzodiazepine,
- 1-(4-Aminophenyl)-8-amino-3,5-dihydro-4-methyl-3-ethylcarbamoyl-7-methoxy-5H-2,3-benzodiazepine,
- 1-(4-Aminophenyl)-8-amino-3,5-dihydro-4-methyl-3-propylcarbamoyl-7-methoxy-5H-2,3-benzodiazepine,
- 1-(4-Aminophenyl)-8-amino-3,5-dihydro-4-methyl-3-butylcarbamoyl-7-methoxy-5H-2,3-benzodiazepine, 1-(4-Aminophenyl)-3,5-dihydro-4-methyl-3-acetyl-8-methoxy-5H-2,3-benzodiazepine,
1-(4-Aminophenyl)-3,5-dihydro-4-methyl-3-methylcarbamoyl-8-methoxy-5H-2,3-benzodiazepine,
1-(4-Aminophenyl)-3,5-dihydro-4-methyl-3-ethylcarbamoyl-8-methoxy-5H-2,3-benzodiazepine,
1-(4-Aminophenyl)-3,5-dihydro-4-methyl-3-propylcarbamoyl-8-methoxy-5H-2,3-benzodiazepine,
1-(4-Aminophenyl)-3,5-dihydro-4-methyl-3-butylcarbamoyl-8-methoxy-5H-2,3-benzodiazepine,
1-(4-Aminophenyl)-7-amino-3,5-dihydro-4-methyl-3-acetyl-8-methoxy-5H-2,3-benzodiazepine,
1-(4-Aminophenyl)-7-amino-3,5-dihydro-4-methyl-3-methylcarbamoyl-8-methoxy-5H-2,3-benzodiazepine,
1-(4-Aminophenyl)-7-amino-3,5-dihydro-4-methyl-3-ethylcarbamoyl-8-methoxy-5H-2,3-benzodiazepine,
1-(4-Aminophenyl)-7-amino-3,5-dihydro-4-methyl-3-propylcarbamoyl-8-methoxy-5H-2,3-benzodiazepine,
1-(4-Aminophenyl)-7-amino-3,5-dihydro-4-methyl-3-butylcarbamoyl-8-methoxy-5H-2,3-benzodiazepine,
1-(4-Aminophenyl)-3,5-dihydro-4-methyl-3-acetyl-7-methylthio-5H-2,3-benzodiazepine,
1-(4-Aminophenyl)-3,5-dihydro-4-methyl-3-methylcarbamoyl-7-methylthio-5H-2,3-benzodiazepine,
1-(4-Aminophenyl)-3,5-dihydro-4-methyl-3-ethylcarbamoyl-7-methylthio-5H-2,3-benzodiazepine,
1-(4-Aminophenyl)-3,5-dihydro-4-methyl-3-propylcarbamoyl-7-methylthio-5H-2,3-benzodiazepine,
1-(4-Aminophenyl)-3,5-dihydro-4-methyl-3-butylcarbamoyl-7-methylthio-5H-2,3-benzodiazepine,
1-(4-Aminophenyl)-8-amino-3,5-dihydro-4-methyl-3-acetyl-7-methylthio-5H-2,3-benzodiazepine,
1-(4-Aminophenyl)-8-amino-3,5-dihydro-4-methyl-3-methylcarbamoyl-7-methylthio-5H-2,3-benzodiazepine,
1-(4-Aminophenyl)-8-amino-3,5-dihydro-4-methyl-3-ethylcarbamoyl-7-methylthio-5H-2,3-benzodiazepine,
1-(4-Aminophenyl)-8-amino-3,5-dihydro-4-methyl-3-propylcarbamoyl-7-methylthio-5H-2,3-benzodiazepine,
1-(4-Aminophenyl)-8-amino-3,5-dihydro-4-methyl-3-butylcarbamoyl-7-methylthio-5H-2,3-benzodiazepine,
1-(4-Aminophenyl)-3,5-dihydro-4-methyl-3-acetyl-8-methylthio-5H-2,3-benzodiazepine,
1-(4-Aminophenyl)-3,5-dihydro-4-methyl-3-methylcarbamoyl-8-methylthio-5H-2,3-benzodiazepine,
1-(4-Aminophenyl)-3,5-dihydro-4-methyl-3-ethylcarbamoyl-8-methylthio-5H-2,3-benzodiazepine,
1-(4-Aminophenyl)-3,5-dihydro-4-methyl-3-propylcarbamoyl-8-methylthio-5H-2,3-benzodiazepine,
1-(4-Aminophenyl)-3,5-dihydro-4-methyl-3-butylcarbamoyl-8-methylthio-5H-2,3-benzodiazepine,
1-(4-Aminophenyl)-7-amino-3,5-dihydro-4-methyl-3-acetyl-8-methylthio-5H-2,3-benzodiazepine,
1-(4-Aminophenyl)-7-amino-3,5-dihydro-4-methyl-3-methylcarbamoyl-8-methylthio-5H-2,3-benzodiazepine,
1-(4-Aminophenyl)-7-amino-3,5-dihydro-4-methyl-3-ethylcarbamoyl-8-methylthio-5H-2,3-benzodiazepine,
1-(4-Aminophenyl)-7-amino-3,5-dihydro-4-methyl-3-propylcarbamoyl-8-methylthio-5H-2,3-benzodiazepine, and
1-(4-Aminophenyl)-7-amino-3,5-dihydro-4-methyl-3-butylcarbamoyl-8-methylthio-5H-2,3-benzodiazepine.

B. Compounds of Formula II

Compounds of Formula II are provided which are active as non-NMDA ionotropic EAA receptor antagonists.

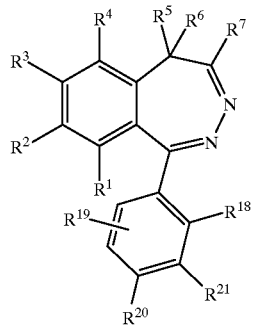

where
$R^1$, $R^2$, $R^3$ and $R^4$ are independently
H,
HO,
$R^{13}O-$,
halogen (F, Cl, Br),
C1–C3-alkyl,
$CF_3$,
$R^{14}CO_2-$,
$R^{14}O_2C-$,
$R^{14}CO-$,
$R^{14}CONH-$,
$R^{14}NHCO-$,
$R^{14}NHCO_2-$,
$R^{14}OCONH-$,
$R^{14}O_2S-$,
$R_{14}OS-$, or
$R^{15}R^{16}N-$; or $R^1$ and $R^2$, or $R^2$ and $R^3$, or $R^3$ and $R^4$ taken together can be
$-SCH_2S-$,
$-SCH_2O-$,
$-OCH_2S-$,
$-SCH_2CH_2S-$,
$-SCH_2CH_2O-$, or
$-OCH_2CH_2S-$; or one of four substitutents of $R^1$, $R^2$, $R^3$ and $R^4$ must be C1–C3-alkoxy or C1–C3-alkylthio group;

$R^5$, $R^6$, and $R^7$ are independently
H,
C1–C6-alkyl,
C3–C6-alkenyl,
C3–C6-cycloalkyl, or
phenyl or substituted phenyl, where the phenyl is substituted with one or two substituents, C1–C3-alkyl, halogen (F, Cl, Br), $R^{13}O-$, $CF_3-$, $R^{14}O_2S-$, $R^{14}OS-$, $R^{14}CO$, $R^{14}CO_2-$, $R^{14}O_2C-$, $R^{14}CONH-$, $R^{14}NHCO$; or $R^5$ and $R^6$ taken together can be C3–C6-cycloalkyl;

$R^{13}$ is C1–C3-alkyl;

$R^{14}$ is H or C1–C3-alkyl;

$R^{15}$ and $R^{16}$ are independently
H,
C1–C10-alkyl,
C1–C6-perfluoroalkyl,
C3–C10-alkenyl, or
C3–C6-cycloalkyl; or $R^{15}$ and $R^{16}$ taken together can be C3–C6-cycloalkyl;

$R^{17}$ is C1–C6-alkyl, C3–C6-alkenyl, or C3–C6-cycloalkyl;

$R^{18}$ and $R^{19}$ are independently
H,
halogen (F, Cl, Br),
C1–C3-alkyl,
$R^{14}O$—,
$CF_3$—, or
$R^{14}CO_2$—;
$R^{20}$ and $R^{21}$ are independently
H,
$R^{15}R^{16}N$—,
$R^{15}HNC(NH)$—, or
$R^{14}CONH$—;
and pharmaceutically acceptable salts thereof;
where $R^{20}$ and $R^{21}$ cannot both be H.
Preferred compounds are compounds of Formula II where:
one of four substitutents of $R^1$, $R^2$, $R^3$ and $R^4$ must be C1–C3-alkylthio or C1–C3-alkoxy group, the other substituents are independently H, $R^{13}O$—, $R^{13}S$—, halogen (F, Cl, Br), or C1–C3-alkyl;
$R^2$ and $R^3$ taken together can be —SCH$_2$S—, —SCH$_2$O—, or OCH$_2$S—;
$R^{20}$ and $R^{20}$ are independently H, $H_2N$—, or $CH_3CONH$—; and pharmaceutically acceptable salts thereof.
Specifically preferred are:
1-(4-Aminophenyl)-4-methyl-7-methoxy-5H-2,3-benzodiazepine,
1-(4-Aminophenyl)-8-amino-4-methyl-7-methoxy-5H-2,3-benzodiazepine,
1-(4-Aminophenyl)-4-methyl-8-methoxy-5H-2,3-benzodiazepine,
1-(4-Aminophenyl)-7-amino-4-methyl-8-methoxy-5H-2,3-benzodiazepine,
1-(4-Aminophenyl)-4-methyl-7-methylthio-5H-2,3-benzodiazepine,
1-(4-Aminophenyl)-8-amino-4-methyl-7-methylthio-5H-2,3-benzodiazepine,
1-(4-Aminophenyl)-4-methyl-8-methylthio-5H-2,3-benzodiazepine, and
1-(4-Aminophenyl)-7-amino-4-methyl-8-methylthio-5H-2,3-benzodiazepine.

The compounds of Formulas I and II may be combined with a suitable pharmaceutical carrier and used to treat neurological, neuropsychological, neuropsychiatric, neurodegenerative, neuropsychopharmacological and functional disorders associated with excessive activation of the non-NMDA subtype of the ionotropic EAA receptors. The compounds can also be used as testing agents to identify and characterize other compounds for the treatment of acute and chronic neurodegenerative diseases, seizures, depression, anxiety and substance addiction.

Pharmaceutically acceptable salts include both the metallic (inorganic) salts and organic salts; a list of which is given in Remington's Pharmaceutical Sciences 17th Edition, p. 1418 (1985). It is well known to one skilled in the art that an appropriate salt form is chosen based on physical and chemical stability, flowability, hygroscopicity and solubility.

III. Synthesis

The compounds of Formula I or II may be prepared using synthetic reactions and techniques available in the art, as described, for example in March, "Advanced Organic Chemistry," 4$^{th}$ Edition, 1992, Wiley-Interscience Publication, New York. The reactions are performed in solvents suitable to the reagents and materials employed and suitable for the transformation being effected. Depending upon the synthetic route selected, and the functionality of the starting material or intermediates, the appropriate protection groups and deprotection conditions available in the art of organic synthesis may be utilized in the synthesis of the compound.

In one embodiment, compounds of Formula I and II may be synthesized as outlined in Schemes 1–3.

Compounds with 7-alkoxy or 7-alkylthio substituents may be synthesized as outlined in Scheme 1.

Ketone 1 gave alcohols 2 by reduction with sodium borohydride in a solvent such as methanol at a temperature of 0° to 30° C. for 1–8 hours. Acid-catalyzed reaction of 2 with 4-nitrobenzaldehydes led to 3, which was oxidazied by air in DMF/DMSO to semiketal 4. Reaction of semiketal 4 with acetic hydrazide in refluxing ethanol gave hydrazones 5. Treatment of 5 with methanesulfonyl chloride and triethylamine gave mesylates 6. The mesylates 6 were treated with lithium tert-butoxide in THF to give cyclized product 7. The nitro groups of 7 were reduced by catalytic hydrogenation to give desired product 8.

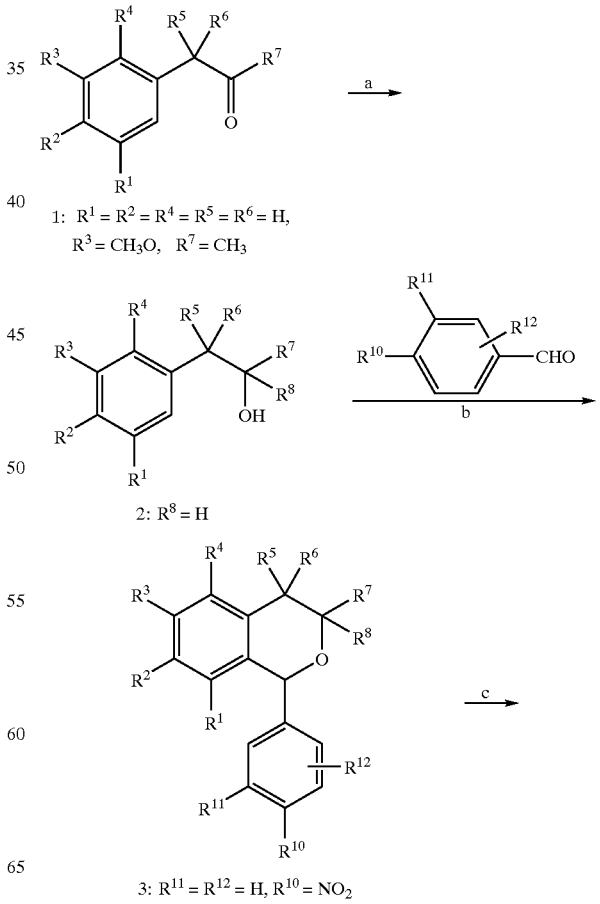

Scheme 1

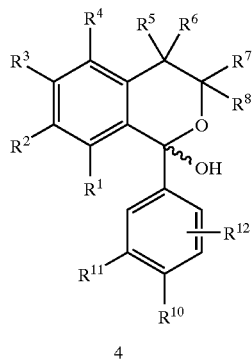

4

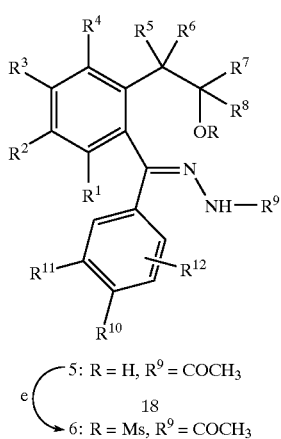

5: R = H, R⁹ = COCH₃
6: R = Ms, R⁹ = COCH₃
18

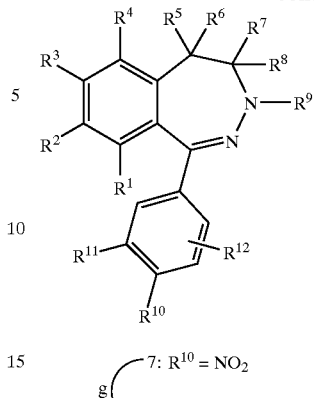

7: R¹⁰ = NO₂
8: R¹⁰ = NH₂

Reaction conditions: (a) NaBH₄, MeOH, 0° C.; (b) HCl in dioxane, reflux; (c) air, DMF/DMSO, -5° C.; (d) H₂NNHAc/EtOH, catalytic HCl, reflux; (e) MsCl/Et₃N/DCM, -5° C.; (f) ᵗBuOLi/THF, 0° C.; (g) H₂, Pd/C, EtOAc.

Compounds with 8-alkoxy or 8-alkylthio substituents may be synthesized as outlined in Scheme 2.

Nitration of compound 9 gave compound 10. The nitro groups of 10 were reduced by catalytic hydrogenation to give aniline 11, which was converted to amide 12, by reaction with acetic anhydride. Ketone 12 gave alcohols 13 by reduction with sodium borohydride in a solvent such as methanol at a temperature of 0° to 30° C. for 1–8 hours. Acid-catalyzed reaction of 13 with 4-nitrobenzaldehydes led to 14, which were deprotected, with 4N H₂SO₄ in methanol to give aniline 15. The amine group in 15 was removed by first converting to diazonium, then decomposing the diazonium with H₃PO₂ to give compound 16. Compound 16 was oxidazied by air in DMF/DMSO to semiketal 17. Reaction of semiketal 17 with acetic hydrazide in refluxing ethanol gave hydrazones 18. Treatment of 18 with methanesulfonyl chloride and triethylamine gave mesylates 19. The mesylates 19 were treated with lithium tert-butoxide in THF to give cyclized product 20. The nitro groups of 20 were reduced by catalytic hydrogenation to give desired product 21.

Scheme 2

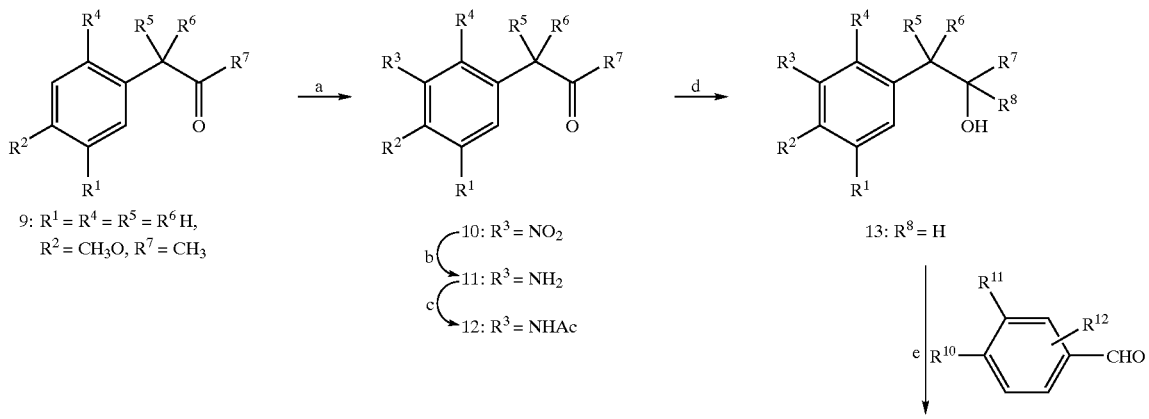

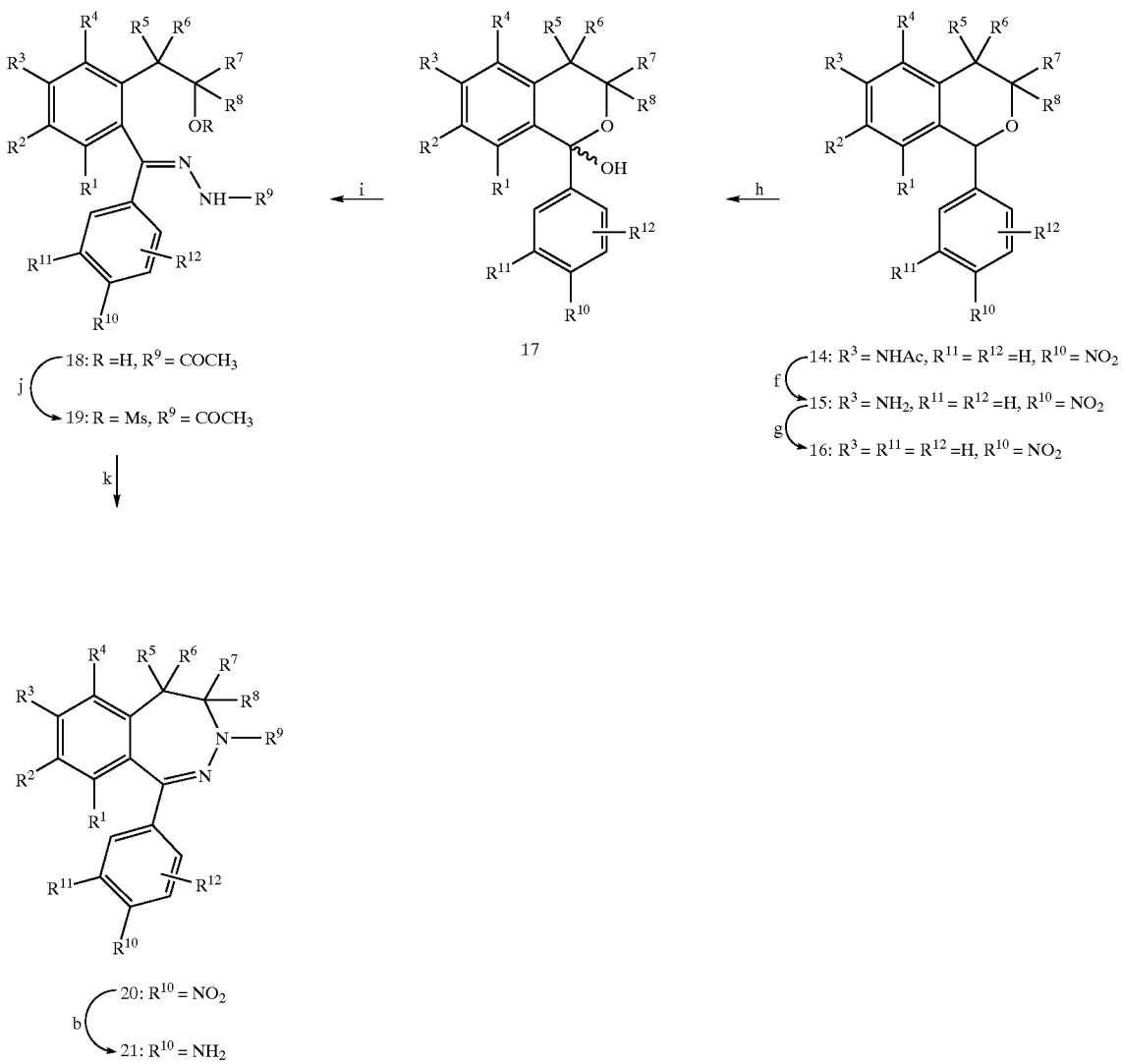

Reaction conditions: (a) HNO₃, AcOH, 0° C.; (b) H₂, Pd/C, EtOAc;
(c) Ac₂O, CHCl₃; (d) NaBH₄, MeOH; (e) HCl in dioxane, reflux;
(f) 4N H₂SO₄, MeOH; (g) (1) H₂SO₄, NaNO₂, 0° C., (2) H₃PO₂, reflux;
(h) air, DMF/DMSO, -5° C.; (i) H₂NNHAc, EtOH, catalytic HCl, reflux;
(j) MsCl, Et₃N, DCM, -5° C.; (k) ᵗBuOLi in THF, 0° C.

Compounds with 8-alkoxy or 8-alkylthio and 7-amino substituents may be synthesized as outlined in Scheme 3.

Compound 14 was oxidazied by air in DMF/DMSO to semiketal 22. Reaction of semiketal 22 with acetic hydrazide in refluxing ethanol gave hydrazones 23. Treatment of 23 with methanesulfonyl chloride and triethylamine gave mesylates 24. The mesylates 24 were treated with lithium tert-butoxide in THF to give cyclized product 25. Amide 25 was hydrolyzed to give aniline 26, which was reduced by catalytic hydrogenation to give desired product 27. Compound 14 was oxidazied to diketone 28, which was treated with hydrazine with concomitant N-deacetylation to give benzodiazepine 29.

Scheme 3

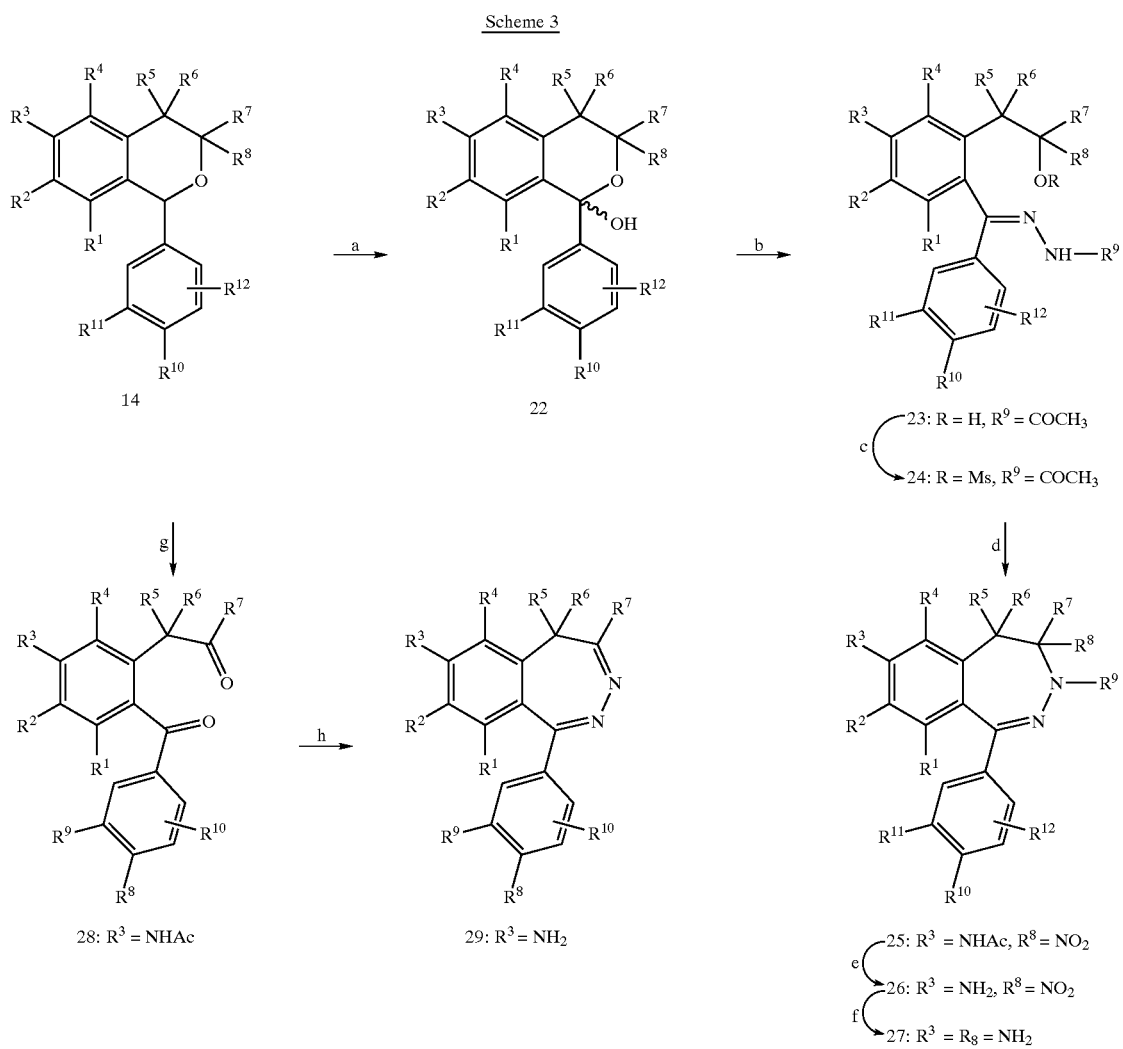

Reaction conditions: (a) air, DMF/DMS, -5° C.; (b) H$_2$NNHAc/EtOH, catalytic HCl, reflux; (c) MsCl, Et$_3$N, DCM, -5° C.; (d) $^t$BuOLi in THF, 0° C.; (e) NaOH, MeOH; (f) H$_2$, Pd/C, EtOAc; (g) acetone, CrO$_3$ in 35% H$_2$SO$_4$; (h) NH$_2$NH$_2$·H$_2$O, EtOH, reflux.

IV. In Vitro and In Vivo Assays of Activity and Therapeutic Efficacy

In vivo and in vitro assays may be conducted to determine the activity of the compounds as antagonists of the non-NMDA receptors, i.e., the ionotropic EAA receptors which bind AMPA or KA. In combination, in vitro and in vivo assays are predictive of the activity of these compounds for treatment of patients. This is supported, for example, by numerous studies in the literature illustrating that in vitro and in vivo studies of NMDA receptor modulation by a test compound provide a good indication of the compound's efficacy in treating disorders associated with excessive activation of the NMDA receptor. See, for example: Meldrum, *Epilepsy Research*, 12:189–196 (1992); Lipton and Rosenberg, *New England Journal of Medicine*, 330:613–622 (1994); and McBurney, *Neurobiology of Aging*, 15:271–273 (1994).

A. Electrophysiology

The potency of the disclosed compounds for drug inhibition of the AMPA receptor can be tested using the whole-cell patch clamp technique on primary cultures of rat neocortex. The general procedure for stimulating AMPA-receptor mediated currents with KA and for the measurement of current inhibition is based on that used by Donevan and Rogawski (*Neuron*, 10: 51–59, 1993) for 2,3-benzodiazepines.

Standard extracellular bath solutions and intracellular pipette solutions are used as described in detail by Hussy and coworkers (*J. Physiol.* (Lond.), 481.2: 311–323,1994). The drug application system is designed to allow rapid switching between 7 different reservoirs containing either control bath solution, kainic acid (50 $\mu$M), or kainic acid (50 $\mu$M) plus antagonist (10 $\mu$M). Each recording is begun with a control response to KA alone.

Following the establishment of a 2–3 sec duration steady baseline, bathing solution is switched to one containing KA plus antagonist for an additional 2–3 sec period. Alternatively, 5 different doses of a single compound are tested for the determination of the antagonist IC$_{50}$.

B. Neurodegenerative Transient Global Forebrain Ischemia

The extent of protection by a test compound in a model of brain ischemia may be assayed as described by Meldrum et al. (*Brain Res.*, 571:115, 1992), and references cited therein. Male Wistar rats (250–300 g) are anesthetized using halothane-oxygen-nitrogen mixture and both vertebral arteries are permanently occluded by electrocauterisation within the alar foraminae of the first cervical vertebra. At the same time, both common carotid arteries are isolated and atraumatic clamps placed around each one. One femoral vein is cannulated to enable the subsequent iv administration of fluid. The following day cerebral ischemia is induced in the unanaesthetised animal, by tightening the clamps around the carotid arteries for 20 min. Carotid clamping results. Body temperature is maintained at 37° C. by use of a rectal probe and hot plate. Seven days after the ischemic insult rats are sacrificed and the brains processed for light microscopy. Neuroprotection is assessed by examination of the extent of damage in the cortex and hippocampus. Compounds may be selected which are active in this model.

C. Neurodegenerative Permanent Focal Ischemia

The extent of protection by a test compound in a model of brain ischemia may be tested using a model described by Meldrum and Smith (*Stroke*, 23:861, 1992), and references cited therein. Male Fisher F344 rats (210–310 g) are anesthetized with halothane-oxygen-nitrogen mixture receive a small incision between the eye and ear, the mandibular muscles are retracted to expose the orbit and zygomatic arch. A small craniotomy is made to expose the base of the middle cerebral artery. Bipolar coagulation is used to permanently occlude the artery at the base. One day after the ischemic insult rats are sacrificed and the brains processed for light microscopic examination. Lesion volume is determined by using Cavalarei's principle. Compounds may be selected which are active in this model.

D. Maximum Electro Shock (MES) Seizure Test

The extent of protection by a test compound in a seizure model is tested as described by Rogawski et al. (*Epilepsy Research*, 15:179–184, 1993). Male NIH Swiss mice (25–30 g) are injected ip with the test drug. The mice are subjected to a 0.2 sec, 60 Hz, 50 mA electrical stimulus delivered with corneal electrodes wetted with 0.9% saline at 15–30 min post dosing. Animals failing to show tonic hind limb extension are scored as protected. Compounds may be selected which are active in this model.

E. Subcutaneous Metrazol (scMET) Seizure Test

This test can be used to determine the extent of protection by a test compound in a seizure model. The method used is that of Chen et al. (*Proc. Soc. Exp. Biol. Med.*, 87:334, 1954). Mice are randomly assigned to vehicle or treatment groups of 3–10 animals per group and then dosed accordingly. Metrazol (pentylenetetrazol) 90 mg/kg is administered subcutaneously (sc) at different time points (0.25, 0.5, 1, 2, 4 hr) after the treatment or control groups. The mice individually housed in clear runs and observed for the presence or absence of clonic seizure activity (>5 s duration) for 30 min after metrazol dosing. A compound is considered active if no seizure is observed. Data is analyzed using a quantal measure (protection/number tested).

V. Dosage Forms

The disclosed compounds can be administered parenterally, that is, subcutaneously, intramuscularly, or intravenously and, alternatively, administered orally, in a dose range of between about 0.01 and 100 mg/kg body weight.

The active ingredient can be administered parenterally in sterile liquid dosage forms. In general, water, a suitable oil, saline, aqueous dextrose, and related sugar solutions and glycols such as propylene glycol or polyethylene glycols are suitable carriers for parenteral solutions. Solutions for parenteral administration preferably contain a water soluble form of the active ingredient, suitable stabilizing agents, and, if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propylparaben, and chlorobutanol.

The active ingredient can be administered orally in solid dosage forms, such as capsules, tablets and powders, or in liquid dosage forms, such as elixirs, syrups, and suspensions. Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. The active ingredients also may be provided in a particle for sustained or pulsed delivery such as a liposome or microcapsule. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. Suitable pharmaceutical carriers are described in Remington's Pharmaceutical Sciences, a standard reference text in this field.

Optionally, the compounds either alone or in combination with a carrier may be administered by implantation or by application to a mucosal surface, for example, the nasal-pharyngeal region and/or lungs using an aerosol or may be administered to a skin surface via a topical carrier such as a cream or lotion.

The compounds of this invention and their preparation can be understood further by the following non-limiting examples which describe the synthesis of exemplary compounds. In these examples, unless otherwise indicated, all temperatures are in degrees Celsius and parts and percentages are by weight.

EXAMPLES

The following examples show the synthesis of compounds 2 through 8 as shown in Scheme 1.

Example 1

Synthesis of 1-(3-Methoxyphenyl)-2-propyl alcohol (2)

To a solution of 3-methoxyphenylacetone (1, 1.0 g) in methanol (30 ml) was added $NaBH_4$ (360 mg) in portions in the period of 20 min at 0° C. The resulting solution was stirred at such temperature for another 40 min. No more starting materials were detected from TLC. Ice water was added to the reaction slowly. It was extracted with $CHCl_3$ three times. The combined organic phase was washed with brine, and dried over $Na_2SO_4$. Removal of the solvent afforded the crude product. Purification of the crude product by using a silica gel column gave the desired product 2 (1.01 g, 100%).

Example 2

Synthesis of 3-Methyl-1-(4-nitrophenyl)-6-methoxyisochroman (3)

To a solution of 1-(3'-methoxyphenyl)-2-propyl alcohol 2 (0.98 g, 5.8 mmol) in 25 ml of HCl solution in 1,4-dioxane was added 4-nitrobenzaldehyde (0.91 g, 6.0 mmol) in one portion. The solution was refluxed for 4 hours. After removing the solvent under reduced pressure, the residue was washed with cold ethanol three times, affording the product 3 (1.62 g, yield 90%). $^1$HNMR(CDCl$_3$): 8.20 (d, J=8.7 Hz, 2H), 7.50 (d, J=8,7 Hz, 2H), 6.65–6.48 (m, 3H), 5.78 (s, 1H), 4.01 (m, 1H), 3.76 (s, 3H), 2.80 (m, 2H), 1.40 (d, J=6.1 Hz).

Example 3

Synthesis of 1-Hydroxy-3-methyl-1-(4-nitrophenyl)-6-methoxyisochroman (4)

A solution of 3 (1.3 g) in 4 ml of DMSO and 24 ml of DMF was cooled to 8–12° C. and air was passed through the mixture. To the solution was added 1.2 ml of 50% aqueous sodium hydroxide in one portion and the resulting mixture was stirred for 5 hours. HCl (1 N) was added, and extracted with ethyl acetate three times. The combined organic phase was washed with water in order to remove DMF, dried over Na$_2$SO$_4$. Removal of the solvent afforded syrup crude product (1.6 g), which was used directly for the next step.

Example 4

Synthesis of 6'-(2-Hydroxypropyl)-4'-methoxy-4-nitrobenzophenone acetylhydrazone (5)

To a solution of 4 (1.6 g) in 25 ml of ethanol was added acetic hydrazide (0.4 g) and 2 drops of concentrated HCl. The resulting solution was heated to reflux for 3 hours. The solvent was removed under reduced pressure. The residue was treated with NaHCO$_3$, and extracted with ethyl acetate. The combined organic phase was washed with brine, dried over Na$_2$SO$_4$. Removal of the solvent gave the desired product (1.25 g).

Example 5

Synthesis of 6'-(2-Methanesulfonyloxypropyl)-4'-methox)-4-nitrobenzophenone acetylhydrazone (6)

To a solution of 5 (0.57 g) in 20 ml of CH$_2$Cl$_2$ was added 0.75 ml of triethyl amine, 0.32 ml of methanesulfonyl chloride at 0–10° C. After 30 min, no more starting material was detected from TLC. Water was added, extracted with CH$_2$Cl$_2$. The organic phase was washed with HCl (1N), brine, dried over Na$_2$SO$_4$. Removal of the solvent afforded product 6 (0.61 g).

Example 6

Synthesis of 3-Acetyl-3,5-dihydro-4-methyl-7-methoxy-1-(4-nitrophenyl)-5H-2,3-benzodiazepine (7)

To a solution of the mesylate 6 (0.56 g) in 10 ml of THF was added lithium tert-butoxide (2.3 ml, 1M) at 0° C. The mixture was warmed to room temperature and stirred for 4 hours. The reaction was quenched by adding a saturated NH$_4$Cl solution. The mixture was diluted with ethyl acetate and washed with water and brine. The organic phase was dried over Na$_2$SO$_4$. Removal of the solvent gave the crude product. Purification of the crude product by silica afforded the desired product 7 (0.36 g.) $^1$HNMR (CDCl$_3$): 8.25 (d, J=9.0 Hz, 2H), 7.73 (d, J=9.0, 2H), 7.00–6.75 (m, 3H), 5.45 (m, 1H), 3.88 (s, 3H), 3.15–2.83 (m, 2H), 2.32 (s, 3H), 1.05 (d, J=6.6 Hz, 3H).

Example 7

Synthesis of 1-(4-Aminophenyl)-3-acetyl-3,5-dihydro-4-methyl-7-methoxy-5H-2,3-benzodiazepine (8)

The mixture of 7 (0.32 g, 0.91 mmol) and 10% palladium on carbon (0.2 g), and ethanol (25 ml) was stirred under hydrogen for 1.5 hours. Filtration of the catalyst and evaporation of solvent gave desired product 8 (0.27 g, yield, 92%) as yellow solid. $^1$HNMR(CDCl$_3$): 7.50 (d, J=9.0 Hz, 2H), 7.0 (m, 1H), 6.80 (m, 2H), 6.69 (d, J=9.0 Hz, 2H), 5.26(m, 1H), 4.0 (br, 2H), 3.83 (s, 3H), 2.70 (m, 2H), 2.0 (s, 3H), 1.32 (d, J=6.4 Hz, 3H).

The following examples show the synthesis of compounds 10 through 21 as shown in Scheme 2.

Example 8

Synthesis of 4-Methoxy-3-nitrophenylacetone (10)

To a solution of 4-methoxyphenylacetone 9 (6.56 g, 4 mmol) in acetic anhydride (16 mmol) was added 90% HNO$_3$ dropwise at −5° C. After adding HNO$_3$, the ice-bath was removed and allowed to warm up to room temperature. The reaction was quenched by adding ice water. The resulting solution was extracted with ethyl acetate three times. The organic phase was dried over Na$_2$SO$_4$. Removal of the solvent under reduced pressure afforded crude product. Purification of the crude product by using silica gel column gave 10 (4.9 g, 59%). $^1$HNMR(CDCl$_3$): 7.70 (d, J=2.1 Hz, 1H), 7.37 (dd, J=2.2 Hz, 8.5 Hz, 1H), 7.08 (d, J=8.5 Hz, 1H), 3.95 (s, 3H), 3.74 (s, 2H), 2.21 (s, 3H).

Example 9

Synthesis of 3-Amino-4-methoxyphenylacetone (11)

The mixture of compound 10 (3.0 g, 14.3 mmol) and 10% palladium on carbon (1.6 g) in ethanol (230 ml) was stirred under hydrogen for 3 hours. Filtration of the catalyst and evaporation of solvent gave desired product 11 (2.41 g, 94%).

Example 10

Synthesis of 3-Acetylamino-4-methoxyphenylacetone (12)

To the mixture of compound 11 (0.25 g, 1.39 mmol) in chloroform (30 ml) was added acetic anhydride (1.2 ml) and catalytic amount of DMAP (10 mg) at 0° C. After stirring at such temperature for 3 hours, no more starting materials were detected on TLC. The reaction was quenched by adding ice water, extracted with CH$_2$Cl$_2$ twice. The organic layer was washed with brine, dried over Na$_2$SO$_4$. Removal of the solvent afforded the crude product. Purification of the crude product by using silica gel column gave 0.3 g (97%) of desired product 12. $^1$HNMR(CDCl$_3$): 8.25 (d, J=1.2 Hz, 1H), 7.79 (br, 1H), 6.81 (m, 2H), 3.86 (s, 3H), 3.64 (s, 2H), 2.20 (s, 3H), 1.95 (s, 3H).

Example 11

Synthesis of 1-(3-Acetylamino-4-methoxyphenyl)-2-propyl Alcohol (13)

To a solution of compound 12 (0.25 g, 1.13 mmol) in methanol was added NaBH$_4$ in portions in the period of 20 min at 0° C. The resulting solution was stirred at such temperature for another 40 min. No more starting materials were detected on TLC. Ice water was added to the reaction slowly. It was extracted with CHCl$_3$ three times. The combined organic phases were washed with brine, and dried over Na$_2$SO$_4$. Removal of the solvent afforded the crude product. Purification of the crude product by using a silica gel column gave the desired product 13 (0.24 g, 95%). $^1$HNMR(CDCl$_3$):

8.24 (d, J=1.8 Hz, 1H), 7.75 (br, 1H), 6.82 (m, 2H), 4.00 (m, 1H), 3.86 (s, 3H), 2.70 (m, 2H), 2.20 (s, 3H), 1.24 (d, J=6.1 Hz, 3H).

Example 12

Synthesis of 6-Acetylamino-3-methyl-1-(4-nitrophenyl)-7-methoxyisochroman (14)

To a solution of compound 13 (0.23 g, 1.03 mmol) in 15 ml of HCl solution in 1,4-dioxane was added 4-nitrobenzaldehyde (0.16 g, 1.06 mmol) in one portion. After refluxing for 5 hours, the solvent was removed under reduced pressure. The residue was washed with cold ethanol three times, and dried to give the product 14 (0.21 g, 66%).

Example 13

Synthesis of 6-Amino-3-methyl-1-(4-nitrophenyl)-7-methoxyisochroman (15)

Solution of 14 (0.114 g, 0.32 mmol) in 5 ml of 4N $H_2SO_4$ and 5 ml of methanol was heated to reflux. After refluxing for 15 hours, the methanol was removed under reduced pressure. The remaining aqueous solution was neutralized with $NaHCO_3$ to pH 9, followed by extraction with ethyl acetate three times. The combined organic phase was dried over $Na_2SO_4$. Removal of the solvent afforded the desired product 15 (100 mg, 100%) which was used directly for next step.

Example 14

Synthesis of 3-Methyl-1-(4-nitrophenyl)-7-methoxyisochroman (16)

Solution of 15 (100 mg, 0.32 mmol) in 5 ml of 4N $H_2SO_4$ was treated with $NaNO_2$ (29.6 mg, 1.16 eq) at 0° C. for 15 min, followed by adding $H_3PO_2$ (50%, 0.25 ml) at such temperature. After refluxing for 5 hours, the solution was extracted with ethyl acetate three times. The combined organic phases were dried over $Na_2SO_4$. Removal of the solvent afforded the crude product. Purification of the crude product by using silica gel column gave the desired product 16 (82 mg, 86%).

Example 15

Synthesis of 1-Hydroxy-3-methyl-1-(4-nitrophenyl)-7-methoxyisochroman (17)

A solution of 16 (1.3 g) in 4 ml of DMSO and 24 ml of DMF was cooled to 8–12° C. and air was passed through the mixture. To the solution was added 1.2 ml of 50% aqueous sodium hydroxide in one portion and the resulting mixture was stirred for 5 hours. HCl (1 N) was added, and extracted with ethyl acetate three times. The combined organic phases were washed with water, dried over $Na_2SO_4$. Removal of the solvent afforded 17 as a syrup (1.6 g), which was used directly for the next step.

Example 16

Synthesis of 6'-(2-Hydroxypropyl))-3'-methoxy-4-nitrobenzophenone Acetylhydrazone (18)

To a solution of 17 (1.8 g) in 25 ml of ethanol was added acetic hydrazide (0.5 g) and 2 drops of concentrated HCl. The resulting solution was heated to reflux for 3 hours. The solvent was removed under reduced pressure. The residue was treated with $NaHCO_3$, and extracted with ethyl acetate. The combined organic phase was washed with brine, dried over $Na_2SO_4$. Removal of the solvent gave the desired product 18 (1.32 g).

Example 17

Synthesis of 6'-(2-Methanesulfonyloxypropyl))-3'-methoxy-4-nitrobenzophenone Acetylhydrazone (19)

To a solution of 18 (1.12 g, 3 mmol) in 20 ml of $CH_2Cl_2$ was added 1.5 ml of triethyl amine, 0.60 ml of methanesulfonyl chloride at 0–10° C. After 30 min, no more starting material was detected on TLC. Water was added, extracted with $CH_2Cl_2$. The organic phase was washed with HCl (1N), brine, dried over $Na_2SO_4$. Removal of the solvent afforded product 19 (1.20 g, 89%).

Example 18

Synthesis of 3-Acetyl-3.5-dihydro-4-methyl-8-methoxy-1-(4-nitrophenyl)-5H-2,3-benzodiazepine (20)

To a solution of the mesylate 19 (1.5 g,) in 80 ml of THF was added lithium tert-butoxide (16.5 ml, 1M) at 0° C. The mixture was warmed to room temperature and stirred for 4 hours. The reaction was quenched by adding a saturated $NH_4Cl$ solution. The mixture was diluted with ethyl acetate and washed with water and brine. The organic phase was dried over $Na_2SO_4$. Removal of the solvent gave the crude product. Purification of the crude product by silica afforded the desired product 20 (0.97 g). $^1HNMR(CDCl_3)$: 8.26 (d, J=9.0 Hz, 2H), 7.75 (d, J=9.0 Hz, 2H), 7.20 (d, J=9.0 Hz, 1H), 6.93 (dd, J=9.0 Hz, 2.1 Hz, 1H), 6.58 (d, J=2.1 Hz, 1H), 5.40 (m, 1H), 3.72 (s, 3H), 3.10–2.80 (m, 2H), 2.36 (s, 3H), 1.00 (d, J=6.0 Hz, 3H).

Example 19

Synthesis of 1-(4-Aminophenyl)-3-acetyl-3.5-dihydro-4-methyl-8-methoxy-5H-2,3-benzodiazepine (21)

The mixture of 20 (0.72 g, 0.91 mmol) and 10% palladium on carbon (0.25 g), and ethyl acetate (40 ml) was stirred under hydrogen for 1.5 hours. Filtration of the catalyst and purification by silica gel gave desired product 21 (0.27 g, 46%) as yellow solid.

$^1HNMR(CDCl_3)$: 7.76(d, J=9.0 Hz, 2H), 7.20 (d, J=7.2 Hz, 1H), 7.0 (d, J=9.0, 2H), 6.86 (d, J=7.2 Hz, 1H), 6.60 (s, 1H), 5.38 (br, 2H), 5.20 (m, 1H), 3.73 (s, 3H), 2.85–2.63 (m, 2H), 2.07 (s, 3H), 1.28 (d, J=6.0 Hz, 3H).

The following examples show the synthesis of compounds 22 through 29 as shown in Scheme 3.

Example 20

Synthesis of 6-Acetylamino-1-hydroxy-3-methyl-1-(4-nitrophenyl)-7-methoxyisochroman (22)

A solution of 14 (1.8 g) in 5 ml of DMSO and 30 ml of DMF was cooled to 8–12° C. and air was passed through the mixture. To the solution was added 1.2 ml of 50% aqueous sodium hydroxide in one portion and the resulting mixture was stirred for 5 hours. HCl (1 N) was added, and extracted with ethyl acetate three times. The combined organic phase was washed with water, dried over $Na_2SO_4$. Removal of the solvent afforded 22 (1.9 g) as a syrup, which was used directly for the next step.

Example 21

Synthesis of 2'-Acetylamino-6'-(2-hydroxypropyl)-3'-methoxy-4-nitrobenzophenone acetylhydrazone (23)

To a solution of 22 (1.7 g) in 25 ml of ethanol was added acetic hydrazide (0.5 g) and 2 drops of concentrated HCl.

The resulting solution was refluxed for 3 hours. The solvent was removed under reduced pressure. The residue was treated with $NaHCO_3$, and extracted with ethyl acetate. The combined organic phases were washed with brine, dried over $Na_2SO_4$. Removal of the solvent gave the desired product 23 (1.25 g).

Example 22

Synthesis of 2'-Acetylamino-6'-(2-methanesulfonyloxypropyl)-3'-methoxy-4-nitrobenzophenone acetylhydrazone (24)

To a solution of 23 (1.1 g) in 20 ml of $CH_2Cl_2$ was added 1.5 ml of triethyl amine, 0.60 ml of methanesulfonyl chloride at 0–10° C. After 30 min, no more starting material was detected on TLC. Water was added, extracted with $CH_2Cl_2$. The organic phase was washed with HCl (1N), brine, dried over $Na_2SO_4$. Removal of the solvent afforded product 24 (1.21 g).

Example 23

Synthesis of 3-Acetyl-7-acetylamino-3.5-dihydro-4-methyl-8-methoxy-1-(4-nitrophenyl)-5H-2,3-benzodiazepine (25)

To a solution of the mesylate 23 (1.15 g, 2.27 mmol) in 15 ml of THF was added lithium tert-butoxide (4.5 ml, 1M) at 0° C. The mixture was warmed to room temperature and stirred for 4 hours. Adding a saturated $NH_4Cl$ solution quenched the reaction. The mixture was diluted with ethyl acetate and washed with water and brine. The organic phase was dried over $Na_2SO_4$. Removal of the solvent gave the crude product. Purification of the crude product by silica afforded the desired product 25 (0.86 g, 92%).

Example 24

Synthesis of 3-Acetyl-7-amino-3.5-dihydro-4-methyl-8-methoxy-1-(4-nitrophenyl)-5H-2,3-benzodiazepine (26)

The solution of acetyl amide 25 (0.8 g, 1.95 mmol) in 20 ml of methanol and 10 ml of NaOH (2 N) was refluxed until there is no more starting material left on TLC. The solution was diluted with water, and extracted with $CH_2Cl_2$ three times. Removal of the solvent afforded the crude product, which was purified by using a silica gel column to give the desired product 26 (0.56 g, 78%).

$^1HNMR(CDCl_3)$: 8.25 (d, J=9.0 Hz, 2H), 7.73 (d, J=9.0 Hz, 2H), 7.48 (s, 1H), 7.02 (s, 1H), 6.55 (s, 1H), 5.40 (m, 1H), 3.70 (s, 3H), 3.08 (m, 2H), 2.46 (s, 3H), 1.02 (d, J=6.4 Hz, 3H).

Example 25

Synthesis of 1-(4-Aminophenyl)-3-acetyl-7-amino-3.5-dihydro-4-methyl-8-methoxy-5H-2,3-benzodiazepine (27)

The mixture of compound 26 (0.50 g, 1.36 mmol) and 10% palladium on carbon (0.2 g), and ethanol (20 ml) was stirred under hydrogen for 3.5 hours. Filtration of the catalyst and evaporation of solvent gave desired product 27 (0.30 g, 65%) as yellow solid. $^1HNMR(CDCl_3)$: 7.62 (d, J=8.4 Hz, 2H), 7.49 (s, 1H), 7.10 (br, 2H), 6.83 (d, J=8.4 Hz, 2H), 6.69 (s, 1H), 5.20 (m, 1H), 3.78 (s, 3H), 3.10 (s, 2H), 2.70 (m, 2H), 2.08 (s, 3H), 1.20 (d, J=6.4 Hz, 3H).

Example 26

Synthesis of 3-Acetylamino-4-methoxy-6-(4-nitrobenzoyl)-phenylacetone (28)

To a solution of compound 14 (0.375 g, 1.05 mmol) in 30 ml of acetone was added 3 ml of $CrO_3$ in 35% $H_2SO_4$ at 0° C. The resulted solution was stirred another 2 h at same temperature. Ice water was added. The solution was extracted with ethyl acetate three times. The combined organic phase was washed with brine, followed by drying over Na2SO4. Removal of the solvent afforded the desired product in the yield of 82%. $^1HNMR(CDCl3)$: 8.5–7.8 (m, 6H), 6.8 (s, 1H), 4.08 (s, 2H), 3.8 (s, 3H), 2.24 (s, 3H), 2.21 (s, 3H).

Example 27

Synthesis of 7-Amino-4-methyl-8-methoxy-1-(4-nitrophenyl)-5H-2,3-benzodiazepine (29)

The solution of 25 (0.3 g, 0.81 mmol) in 30 ml of ethanol and 1.0 ml of $NH_2NH_2.H_2O$ was refluxing until there is no more starting material left from TLC. The solution was diluted with water, and extracted with DCM three times. Removal of the solvent afforded the crude product, which was purified by using a silica gel column, gave the desired 0.17 g in the yield of 65%. $^1HNMR(CDCl3)$: 8.9 (s, 1H), 8.4 (d, 2H), 8.17 (br, 1H), 7.9 (d, 2H), 7.55 (br, 1H), 7.1 (s, 1H), 3.9 (s, 3H), 2.3 (s, 3H).

Example 28

In Vitro and In Vivo Tests for Inhibition of $Ca^{2+}$ Influx into Cortical Cells Stimulated with AMPA Three of the antagonists disclosed herein were tested, in vitro, for inhibition of $Ca^{2+}$ influx into cortical cells stimulated with AMPA. They are 1-(4-Aminophenyl)-3,5-dihydro-4-methyl-3-acetyl-7-methoxy-5H-2,3-benzodiazepine (8) (SYM 2267), 1-(4-Aminophenyl)-3,5-dihydro-4-methyl-3-acetyl-8-methoxy-5H-2,3-benzodiazepine (21) (SYM 2268), and 1-(4-Aminophenyl)-3,5-dihydro-4-methyl-3-acetyl-7-amino-8-methoxy-5H-2,3-benzodiazepine (27) (SYM 2269), respectively. The in vitro test measures inhibition of $Ca^{2+}$ influx into cortical cells stimulated with 50 M AMPA by the test compounds. The rationale underlying this assay is that stimulation of the cortical cells with AMPA activates AMPA receptors causing $Ca^{2+}$ influx with an increase in intracellular $Ca^{2+}$ which is then detected by measuring an increase in fluorescence. The $Ca^{2+}$ increase comes mostly from extracellular (influx of $Ca^{2+}$ through the channel into the cell), but could also come from intracellular sources (release of $Ca^{2+}$ from storage). The inhibition of the AMPA receptor function is detected by a decrease in the level of intracellular $Ca^{2+}$ and a decrease in fluorescence. The results are summarized in Table 1.

TABLE 1

Inhibition of $Ca^{2+}$ Influx into Cortical Cells with 50 $\mu M$ AMPA

| Compound | $IC_{50}$ ($\mu M$) |
| --- | --- |
| SYM 2267 | 26.1 |
| SYM 2268 | 16.6 |
| SYM 2269 | 7.3 |

Of the three compounds tested, SYM 2269 ($IC_{50}$=7.3 $\mu M$) is the most potent one for inhibiting AMPA receptor function on cortical neurons in culture.

SYM 2267 was evaluated for in vivo anticonvulsant activity in the maximal electro shock (MES) model in rats. The rats were given the compound orally (PO) ad were found to be fully protected from the MES seizures at 30 mg/kg. No sedative or toxic side effects were observed in the rotorod test. Further tests indicated that SYM 2267 has a MES effective dosage of 8.4 mg/kg ($ED_{50}$=8.4 mg/kg).

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "the compound" is a reference to one or more compounds and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A compound of Formula I:

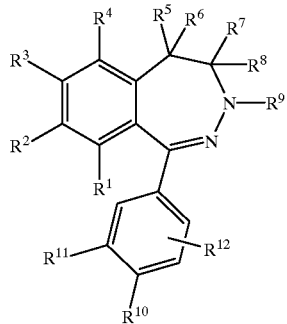

wherein
$R^1$, $R^2$, $R^3$ and $R^4$ are independently
H,
HO,
$R^{13}O-$,
$R^{13}S-$,
halogen,
C1–C3-alkyl,
$CF_3$,
$R^{14}CO_2-$,
$R^{14}CO-$
$R^{14}CONH-$,
$R^{14}NHCO-$,
$R^{14}NHCO_2-$,
$R^{14}OCONH-$,
$R^{14}O_2S-$,
$R^{14}OS-$, or
$R^{15}R^{16}N-$; or
$R^1$ and $R^2$, or $R^2$ and $R^3$, or $R^3$ and $R^4$ taken together can be
$-SCH_2S-$,
$-SCH_2O-$,
$-OCH_2S-$,
$-SCH_2CH_2S-$,
$-SCH_2CH_2O-$, or
$-OCH_2CH_2S-$;
wherein one of $R^1$, $R^3$ and $R^4$ must be C1–C3-alkoxy or C1–C3-alkylthio group;
$R^5$, $R^6$, $R^7$ and $R^8$ are independently
H,
C1–C6-alkyl,
C3–C6-alkenyl,
C3–C6-cycloalkyl,
phenyl or substituted phenyl, wherein the phenyl is substituted with one or two substituents, C1–C3-alkyl, halogen, $R^{13}O-$, $CF_3-$, $R^{14}O_2S-$, $R^{14}OS-$, $R^{14}CO-$, $R^{14}CO_2-$, $R^{14}O_2C-$, $R^{14}CONH-$, $R^{14}NHCO-$; or
$R^5$ and $R^6$ taken together can be C3–C6-cycloalkyl;
$R^7$ and $R^8$ taken together can be C3–C6-cycloalkyl;
$R^9$ is
$R^{15}R^{16}NCO-$,
$R^{15}R^{16}NCS-$,
$R^{17}OCO-$,
$R^{15}CO-$,
$R^{15}R^{16}NCH_2CO-$,
$R^{14}O_2C-(CH_2)_n-$,
$R^{15}R^{16}NCO-(CH_2)_n-$,
$NC-(CH_2)_n-$,
H
C1–C6-alkyl,
C3–C6-alkenyl, or
C3–C6-cycloalkyl; or
$R^8$ and $R^9$ taken together can be
$-(CH_2)_mCH_2(R^{15})NCO-$,
$-(CH_2)_mCH_2OCO-$, or
$-(CH_2)_mCH_2CH_2CO-$;
$R^{10}$ and $R^{11}$ are independently
H,
$R^{15}R^{16}N-$,
$R^{14}HNCO-$, or
$R^{14}CONH-$;
$R^{12}$ is
H,
halogen,
HO,
$R^{13}O-$,
$R^{15}R^{16}N-$,
C1–C3-alkyl,
$CF_3$,
$R^{14}CO_2-$,
$R^{14}CO-$, or
$R^{14}CONH-$;
$R^{13}$ is C1–C3-alkyl;
$R^{14}$ is H or C1–C3-alkyl;
$R^{15}$ and $R^{16}$ are independently
H,
C1–C10-alkyl,
C1–C6-perfluoroalkyl,
C3–C10-alkenyl, or
C3–C6-cycloalkyl; or
$R^{15}$ and $R^{16}$ taken together can be C3–C6-cycloalkyl;
$R^{17}$ is C1–C6-alkyl, C3–C6-alkenyl, or C3–C6-cycloalkyl;
n is 1 to 6;
m is 0 to 2;
and pharmaceutically acceptable salts thereof;
wherein $R^{10}$ and $R^{11}$ cannot be both H.

2. The compound of claim 1 of Formula I wherein one of the substituents of $R^1$, $R^3$ and $R^4$ must be C1–C3-alkylthio group or C1–C3-alkoxy group, the other substituents are independently H, $R^{13}O—$, $R^{13}S—$, halogen, or C1–C3-alkyl;

$R^2$ and $R^3$ taken together can be $—SCH_2S—$, $SCH_2O—$, or $—OCH_2S—$;

$R^9$ is
$R^{15}R^{16}NCO—$,
$R^{15}R^{16}NCS—$,
$R^{17}OCO—$,
$R^{15}CO—$, or
H;

$R^{10}$ and $R^{11}$ are independently H, $H_2N—$, or $CH_3CONH—$; and pharmaceutically acceptable salts thereof.

3. A composition comprising the compound of claim 1 and a pharmaceutically acceptable carrier.

4. A composition comprising the compound of claim 2 and a pharmaceutically acceptable carrier.

5. A method for treating a patient suffering from isohemia, epilepsy or stroke, the method comprising administering to the patient, in an effective amount to alleviate the symptoms of the isohemia, epilepsy or stroke, a compound of Formula I:

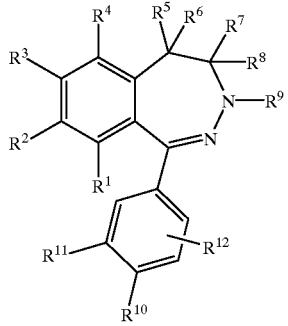

wherein
$R^1$, $R^2$, $R^3$ and $R^4$ are independently
H,
HO,
$R^{13}O—$,
$R^{13}S—$,
halogen,
C1–C3-alkyl,
$CF_3$,
$R^{14}CO_2—$,
$R^{14}O_2C—$,
$R^{14}CO—$,
$R^{14}CONH—$,
$R^{14}NHCO—$,
$R^{14}NHCO_2—$,
$R^{14}OCONH—$,
$R^{14}O_2S—$,
$R^{14}OS—$, or
$R^{15}R^{16}N—$; or
$R^1$ $^{and\ R2}$, or $R^2$ $^{and\ R3}$, or $R^3$ and $R^4$ taken together can be
$—SCH_2S—$,
$—SCH_2O—$,
$—OCH_2S—$,
$—SCH_2CH_2S—$,
$—SCH_2CH_2O—$, or
$—OCH_2CH_2S—$;

wherein one of $R^1$, $R^3$ and $R^4$ must be C1–C3-alkoxy or C1–C3-alkylthio group;

$R^5$, $R^6$, $R^7$ and $R^8$ are independently
H,
C1–C6-alkyl,
C3–C6-alkenyl,
C3–C6-cycloalkyl,
phenyl or substituted phenyl, wherein the phenyl is substituted with one or two substituents, C1–C3-alkyl, halogen, $R^{13}O—$, $CF_3—$, $R^{14}O_2S—$, $R^{14}OS—$, $R^{14}CO—$, $R^{14}CO_2$, $R^{14}O_2C—$, $R^{14}CONH—$, $R^{14}NHCO—$; or $R^5$ and $R^6$ taken together can be C3–C6-cycloalkyl;
$R^7$ and $R^8$ taken together can be C3–C6-cycloalkyl;
$R^9$ is
$R^{15}R^{16}NCO—$,
$R^{15}R^{16}NCS—$,
$R^{17}OCO—$,
$R^{15}CO—$,
$R^{15}R^{16}NCH_2CO—$,
$R^{14}O_2C—(CH^2)_n—$,
$R^{15}R^{16}NCO—(CH_2)_n—$,
$NC—(CH_2)_n—$,
H
C1–C6-alkyl,
C3–C6-alkenyl, or
C3–C6-cycloalkyl; or $R^8$ and $R^9$ taken together can be
$—(CH_2)_mCH_2(R^{15})NCO—$,
$—(CH_2)_mCH_2OCO—$, or
$—(CH_2)_mCH_2CH_2CO—$;

$R^{10}$ and $R^{11}$ are independently
H,
$R^{15}R^{16}N—$,
$R^{14}HNCO—$, or
$R^{14}CONH—$;

$R^{12}$ is
H,
halogen,
HO,
$R^{13}O—$,
$R^{15}R^{16}N—$,
C1–C3-alkyl,
$CF_3$,
$R^{14}CO_2—$,
$R^{14}CO—$, or
$R^{14}CONH—$;

$R^{13}$ is C1–C3-alkyl;
$R^{14}$ is H or C1–C3-alkyl;
$R^{15}$ and $R^{16}$ are independently
H,
C1–C10-alkyl,
C1-C6-perfluoroalkyl,
C3-C10-alkenyl, or
C3–C6-cycloalkyl; or
$R^{15}$ and $R^{16}$ taken together can be C3–C6-cycloalkyl;
$R^{17}$ is C1–C6-alkyl, C3–C6-alkenyl, or C3–C6-cycloalkyl;
n is 1 to 6;
m is 0 to 2;
and pharmaceutically acceptable salts thereof;
wherein $R^{10}$ an $R^{11}$ cannot be both H, in combination with a pharmaceutically acceptable carrier.

6. The method of claim 5 wherein, in the compound of Formula I, one of the substituents of $R^1$, $R^3$ and $R^4$ must be C1–C3-alkylthio group or C1–C3-alkoxy group, the other substituents are independently H, $R^{13}O$—, $R^{13}S$—, halogen, or C1–C3-alkyl;

$R^{2\ and\ R3}$ taken together can be —SCH$_2$S—, —SCH$_2$O—, or —OCH$_2$S—;

$R^9$ is
$R^{15}R^{16}N$ CO—,
$R^{15}R^{16}NCS$—,
$R^{17}OCO$—,
$R^{15}CO$—, or
H;

$R^{10}$ and $R^{11}$ are independently H, H$_2$N—, or CH$_3$CONH—;

and pharmaceutically acceptable salts thereof.

7. A compound of Formula II:

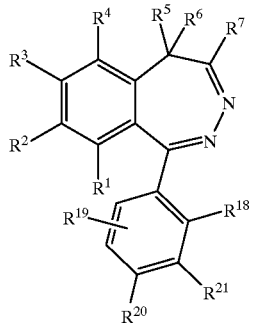

wherein
$R^{1\ and\ R4}$ are independently
H,
HO,
$R^{13}O$—,
$R^{13}S$—,
halogen,
C1–C3-alkyl,
CF$_3$,
$R^{14}CO_2$—,
$R^{14}O_2$—,
$R^{14}CO$—,
$R^{14}CONH$—,
$R^{14}NHCO$—,
$R^{14}NHCO_2$—,
$R^{14}OCONH$—,
$R^{14}O_2S$—,
$R^{14}OS$—, or
$R^{15}R^{16}N$—; or $R^2$ is one of H, HO, $R^{13}O$—, halogen, C1–C3-alkyl, CF$_3$, $R^{14}CO_2$—, $R^{14}O_2C$—, $R^{14}CO$—, $R^{14}CONH$—, $R^{14}NHCO$—, $R^{14}NHCO_2$—, $R^{14}OCONH$—, $R^{14}O_2S$—, $R^{14}OS$—, $R^{13}S$— and $R^{15}R^{16}N$— when $R^3$ is one of HO, halogen, C1–C3-alkyl, CR$_3$, $R^{14}CO_2$—, $R^{14}O_2C$—, $R^{14}CO$—, $R^{14}CONH$—, $R^{14}NHCO$—, $R^{14}NHCO_2$—, R–OCONH—, $R^{14}O_2S$—, $R^{14}OS$—, $R^{13}S$— and $R^{15}R^{16}N$—; or $R^2$ is one of H, HO, halogen, C1–C3-alkyl, CF$_3$, $R^{14}CO_2$—, $R^{14}O_2C$—, $R^{14}CO$—, $R^{14}CONH$—, $R^{14}NHCO$—, $R^{14}NHCO_2$—, $R^{14}OCONH$—, $R^{14}O_2S$—, $R^{14}OS$—, $R^{13}S$— and $R^{15}R^{16}N$— when $R^3$ is one of H, HO, $R^{13}O$—, halogen, C1–C3-alkyl, CF$_3$, $R^{14}CO_2$—, $R^{14}O_2C$—, $R^{14}CO$—, $R^{14}CONH$—, $R^{14}NHCO$—, $R^{14}NHCO_2$—, $R^{14}OCONH$—, $R^{14}O_2S$—, $R^{14}OS$—, $R^{13}S$— and $R^{15}R^{16}N$—; or $R^1$ and $R^2$, or $R^{2\ and\ R3}$, or $R^3$ and $R^4$ taken together can be
—SCH$_2$S—,
—SCH$_2$O—,
—OCH$_2$S—,
—SCH$_2$CH$_2$S—,
—SCH$_2$CH$_2$O—, or
—OCH$_2$CH$_2$S—;

wherein one of the substituents of $R^1$, $R^3$ and $R^4$ must be C1–C3-alkoxy or C1–C3-alkylthio group;

$R^5$, $R^6$ and $R^7$ are independently
H,
C1–C6-alkyl,
C3–C6-alkenyl,
C3–C6-cycloalkyl,
phenyl or substituted phenyl, wherein the phenyl is substituted with one or two substituents, C1–C3-alkyl, halogen, $R^{13}O$—, CF$_3$—, $R^{14}O_2S$—, $R^{14}OS$—, $R^{14}CO$—, $R^{14}CO_2$—, $R^{14}O_2C$—, $R^{14}CONH$—, $R^{14}NHCO$—; or $R^5$ and $R^6$ taken together can be C3–C6-cycloalkyl;

$R^{13}$ is C1–C3-alkyl;

$R^{14}$ is H or C1–C3-alkyl;

$R^{15}$ and $R^{16}$ are independently
H,
C1—C10-alkyl,
C1–C6-perfluoroalkyl,
C3–C10-alkenyl, or
C3–C6-cycloalkyl; or $R^{15}$ and $R^{16}$ taken together can be C3–C6-cycloalkyl;

$R^{18}$ and $R^{19}$ are independently
H,
halogen,
C1–C3-alkyl,
CF$_3$—, or
$R^{14}CO_2$—;

$R^{20}$ and $R^{21}$ are independently
H,
$R^{15}R^{16}N$—,
$R^{15}HNC(NH)$— or
$R^{14}CONH$—;

and pharmaceutically acceptable salts thereof;

wherein $R^{20}$ an $R^{21}$ cannot both be H.

8. The compound of claim 7 of Formula II wherein one of the substituents of $R^1$, $R^3$ and $R^4$ must be C1–C3-alkylthio group or C1–C3-alkoxy group, the other substituents are independently H, $R^{13}O$—, $R^{13}S$—, halogen, or C1–C3-alkyl;

$R^{2\ and\ R3}$ taken together can be —SCH$_2$S—, —SCH$_2$O—, or —OCH$_2$S—;

$R^{20}$ and $R^{21}$ are independently H, H$_2$N—, or CH$_3$CONH—;

and pharmaceutically acceptable salts thereof.

9. A composition comprising the compound of claim 7 and a pharmaceutically acceptable carrier.

10. A composition comprising the compound of claim 8 and a pharmaceutically acceptable carrier.

11. A method for treating a patient, the method comprising administering to the patient, in an effective amount to alleviate the symptoms of the ischemia, epilepsy or stroke, a compound of Formula II:

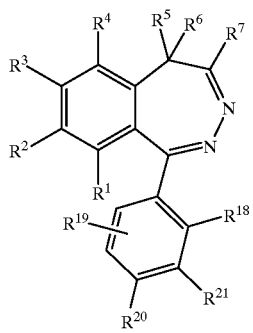

wherein
R$^{1}$ $^{and}$ $^{R4}$ are independently
H,
HO,
R$^{13}$O—,
R$^{13}$S—,
halogen,
C1–C3-alkyl,
CF$_3$,
R$^{14}$CO$_2$—,
R$^{14}$O$_2$C—,
R$^{14}$CO—,
R$^{14}$CONH—,
R$^{14}$NHCO—,
R$^{14}$NHCO$_2$—,
R$^{14}$OCONH—,
R$^{14}$O$_2$S—,
R$^{14}$OS—, or
R$^{15}$R$^{16}$N—; or R$^2$ is one of H, HO, R$^{13}$O—, halogen, C1–C3-alkyl, CF$_3$, R$^{14}$CO$_2$—, R$^{14}$O$_2$C—, R$^{14}$CO—, R$^{14}$CONH—, R$^{14}$NHCO—, R$^{14}$NHCO$_2$—, R$^{14}$OCONH—, R$^{14}$O$_2$S—, R$^{14}$OS— and R$^{15}$R$^{16}$N— when R$^3$ is one of HO, halogen, C1–C3-alkyl, CF$_3$, R$^{14}$CO$_2$—, R$^{14}$O$_2$C—, R$^{14}$CO—, R$^{14}$CONH—, R$^{14}$NHCO—, R$^{14}$NHCO$_2$—, R$^{14}$OCONH—, R$^{14}$O$_2$S—, R$^{14}$OS—, R$^{13}$S— and R$^{15}$R$^{16}$N—; or R$^2$ is one of H, HO, halogen, C1–C3-alkyl, CF$_3$, R$^{14}$CO$_2$—, R$^{14}$O$_2$C—, R$^{14}$CO—, R$^{14}$CONH—, R$^{14}$NHCO—, R$^{14}$NHCO$_2$—, R$^{14}$OCONH—, R$^{14}$O$_2$S—, R$^{14}$OS— and R$^{15}$R$^{16}$N— when R$^3$ is one of H, HO, R$^{13}$O—, halogen, C1–C3-alkyl, CF$_3$, R$^{14}$CO$_2$—, R$^{14}$O$_2$C—, R$^{14}$CO—, R$^{14}$CONH—, R$^{14}$NHCO—, R$^{14}$NHCO$_2$—, R$^{14}$OCONH—, R$^{14}$O$_2$S—, R$^{14}$OS—, R$^{13}$S— and R$^{15}$R$^{16}$N—; or R$^1$ and R$^2$, or R$^2$ $^{and}$ $^{R3}$, or R$^3$ and R$^4$ taken together can be
—SCH$_2$S—,
—SCH$_2$O—,
—OCH$_2$S—,
—SCH$_2$CH$_2$S—,
—SCH$_2$CH$_2$O—, or
—OCH$_2$CH$_2$S—,
wherein one of the substituents of R$^1$, R$^3$ and R$^4$ must be C1–C3-alkoxy or C1–C3-alkylthio group;

R$^5$, R$^6$, and R$^7$ are independently
H,
C1–C6-alkyl,
C3–C6-alkenyl,
C3–C6-cycloalkyl,
phenyl or substituted phenyl, wherein the phenyl is substituted with one or two substituents, C1–C3-alkyl, halogen, R$^{13}$O—, CF$_3$—, R$^{14}$O$_2$S—, R$^{14}$OS—, R$^{14}$CO—, R$^{14}$CO$_2$—, R$^{14}$O$_2$C—, R$^{14}$CONH—, R$^{14}$NHCO—; or R$^5$ and R$^6$ taken together can be C3–C6-cycloalkyl;

R$^{13}$ is C1–C3-alkyl;

R$^{14}$ is H or C1–C3-alkyl;

R$^{15}$ and R$^{16}$ are independently
H,
C1–C10-alkyl,
C1–C6-perfluoroalkyl,
C3–C10-alkenyl, or
C3–C6-cycloalkyl; or R$^{15}$ and R$^{16}$ taken together can be C3–C6-cycloalkyl;

R$^{18}$ and R$^{19}$ are independently
H,
halogen,
C1–C3-alkyl,
R$^{14}$O—,
CF$_3$—, or
R$^{14}$CO$_2$—;

R$^{20}$ and R$^{21}$ are independently
H,
R$^{15}$R$^{16}$N—,
R$^{15}$HNC(NH)— or
R$^{14}$CONH—;

and pharmaceutically acceptable salts thereof;
wherein R$^{20}$ and R$^{21}$ cannot both be H
in combination with a pharmaceutically acceptable carrier.

12. The method of claim 11 wherein, in the compound of Formula II
wherein one of the substituents of R$^1$, R$^3$ and R$^4$ must be C1–C3-alkylthio group or C1–C3-alkoxy group, the other substituents are independently H, R$^{13}$O—, R$^{13}$S—, halogen, or C1–C3-alkyl;

R$_2$ and R$_3$ taken together can be —SCH$_2$S—, —SCH$_2$O—, or —OCH$_2$S—;

R$^{20}$ and R$^{21}$ are independently H, H$_2$N—, or CH$_3$CONH—;
and pharmaceutically acceptable salts thereof.

* * * * *